(12) United States Patent
Lemaux et al.

(10) Patent No.: US 6,541,257 B2
(45) Date of Patent: *Apr. 1, 2003

(54) METHOD FOR PREPARING BARLEY GREEN REGENERATIVE TISSUE

(75) Inventors: Peggy G. Lemaux, Moraga, CA (US); Myeong-Je Cho, Alameda, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/825,217

(22) Filed: Apr. 3, 2001

(65) Prior Publication Data

US 2001/0031496 A1 Oct. 18, 2001

Related U.S. Application Data

(62) Division of application No. 08/845,939, filed on Apr. 29, 1997, now Pat. No. 6,235,529.

(51) Int. Cl.$^7$ .............................. C12N 5/04; C12N 5/02; C12N 15/82; A01N 4/00
(52) U.S. Cl. .................... 435/430.1; 435/410; 435/419; 435/420; 435/430; 435/431; 435/468; 800/278; 800/320
(58) Field of Search .............................. 435/410, 430.1, 435/419, 420, 430, 431, 468; 800/278, 298, 320

(56) References Cited

U.S. PATENT DOCUMENTS

| | | |
|---|---|---|
| 4,699,644 A | 10/1987 | Brandt et al. |
| 5,164,310 A | 11/1992 | Smith et al. |
| 5,281,529 A | 1/1994 | Zhong et al. |
| 5,320,961 A | 6/1994 | Zhong et al. |
| 5,350,688 A | 9/1994 | Matsuno et al. |
| 5,403,736 A | 4/1995 | Tanimoto |
| 5,565,355 A | 10/1996 | Smith |
| 5,589,617 A | 12/1996 | Nehra et al. |
| 5,610,042 A | 3/1997 | Chang et al. |
| 5,641,664 A | 6/1997 | D'Halluin et al. |

FOREIGN PATENT DOCUMENTS

| | | |
|---|---|---|
| EP | 0558676 A | 9/1993 |
| JP | 04027466 | 1/1989 |
| WO | WO 92/20809 | 11/1992 |
| WO | WO 94/13822 | 6/1994 |
| WO | WO 96/04392 | 2/1996 |

OTHER PUBLICATIONS

Baillie et al., Field Evaluation of Barley (*Horedum vulgare* L.) Genotypes Derived from Tissue Culture, *Can. J. Plant. Sci.*, 1992, pp. 725–733, vol. 72.
Bhaskaran et al., Regeneration in Cereal Tissue Culture: A Review, *Crop Sci.*, 1990, pp. 1328–1337, vol. 30.
Bregitzer, Plant Regeneration from Barley Callus: Effects of 2, 4–dischlorophenoxyacetic Acid and Phenylacetic Acid, *Plant Cell Tiss. Org. Cult.*, 1995, pp. 229–235, vol. 43.
Christensen et al., Ubiquitin promoter–Based Vectors for High–Level Expression of Selectable ad/or Screenable Marker Genes in Monocotyledonous Plants, *Transgenic Res.*, 1996, pp. 1–6, vol. 6.
Dahleen, Improved Plant Regeneration from Barley Callus Cultures by Increased Copper Levels, *Plant Cell Tiss. Org. Cult.*, 1995, pp. 267–269, vol. 48.
De Block et al., Engineering Herbicide Resistance in Plants by Expression of a Detoxifying Enzyme, 1987, *EMBO J.*, 1987, pp. 2513–2518, vol. 6.
Fletcher, Retardation of Lea Senescence by Benzyladenine in Intact Bean Plants, *Planta*, 1969, pp. 1–8, vol. 89.
Fromm et al., Stable Transformation of Maize After Gene Transfer b Electroporation, 1986, pp.791–793, vol. 319.
Fromm et al., An Octopine Synthase Enhancer Element Directs Tissue–Specific Expression and Binds ASF–1, a Factor from Tobacco Nuclear Extracts, *Plant Cell*, 1989, pp. 977–984, vol. 1.
Funatsuki et al.,Fertile Transgeneic Barley Generated by Direct DNA Transfer to Photoplasts, *Theor. Appl. Genet.* 1995, pp. 707–712, vol. 91.
Ghaemi et al., The Effects of Silver Nitrate, Colchicine, Cupric Sulfate and Genotype on the Production of Embryoids from Anthers of Tetraploid Wheat (*Triticum turgidum*), *Plant Cell Tiss. Org. Cult.*, 1994, pp. 355–359, vol. 36.
Gless et al., Transgenic Oat Plants Obtained at High Efficiency by Microprojectile Bombardment of Leaf Base Segments, *J. Plant Physiol.*, 1998, pp. 151–157, vol. 152.
Goldstein et al., Tissue Culture and Plant Regeneration from Immature Embryo Explants of Barley, *Hordeum vulagare, Theor. Appl. Genet.*, 1986, pp. 631–636, vol. 71.
Golden–Kamm et al., Transformation of Maize Cells and Regeneration of Fertile Transgenic Plants, *Plant Cell*, 1990, pp. 603–618, vol. 2.
Griffin et al., High–Frequency Plant Regeneration from Seed–Derived Callus Cultures of Kentucky Bluegrass (*Poe pratensis* L.), *Plant Cell Rep.*, 1995, pp. 721–724, vol. 14.
Hagio et al., Production of Fertile Transfenic Barley (*Hordeum vulgare* L.) Plant Using The Hygromycin–Resistance Marker, *Plant Cell Rep.*, 1995, pp. 329–334, vol. 14.
Hanzel et al., Genotype and Media Effects on Callus Formation and Regeneration in Barley, *Crop Sci.* 1985, pp. 27–31, vol. 25.
Holm et al., Regeneration of Fertile Barley Plants from Mechanically Isolated Protoplasts of the Fertilized Egg Cell, *Plant Cell*, pp. 531–543, vol. 6.

(List continued on next page.)

*Primary Examiner*—David T. Fox
*Assistant Examiner*—Russell Kallis
(74) *Attorney, Agent, or Firm*—Morrison & Foerster LLP

(57) ABSTRACT

A method of preparing green regenerative tissue of barley suitable for transformation is presented. The method includes incubating barley tissue on a callus induction medium under dim light. The dim light conditions are sufficient to produce green regenerative tissue. The callus induction media includes auxin and copper.

20 Claims, 1 Drawing Sheet

OTHER PUBLICATIONS

Holtorf et al., Two Routes of Chlorophyllide Synthesis that are Differentially Regulated by Light in Barley (*Hordeum vulgare* L.), *Proc. Natl. Acad. Sci. USA*, 1995, pp. 3254–3258, vol. 92.

Jähne et al., Regeneration of Transgenic, Microspore–Derived, Fertile Barley, *Theor. Appl. Genet.*, 1994, pp. 525–533, vol. 89.

Jain et al., An Improved Procedure for Plant Regeneration from Indica and Japonica Rice Protoplasts, *Plant Cell Reports*.

Kasha et al., Haploids in Cereal Improvement: Anther and Microspore Culture, In: *Gene Manipulation in Plant Improvement II*, Gustafson (ed.), Pienum Press; New York, 1991, pp. 213–235.

Kott et al., Initiation and Morphological Development of Somatic Embryoids from Barley Cell Cultures, *Can. J. Bot.*, 1984, pp. 1245–1249, vol. 62.

Lemaux et al., Bombardment–Mediated Transformation Methods for Barley, *Bio–Rad US/EG Bulletin 2007*, 1996.

Lührs et al., Plant regeneration *In Vitro* from Embryogenic Cultures of Spring– and Winter–Type Barley (*Hordeum vulgare* L.) Varieties, *Theor.*; *Appl. Genet.* 1987, pp. 16–25, vol. 75.

Murakami et al., The Bialaphos Biosynthetic Genes of *Streptomyces Hygroscopicus*: Molecular Cloning and Characterization of the Gene Cluster, *Mol. Gen. Genet.*, 1986, pp. 42–50, vol. 205.

Napoli et al., Introduction of a Chemeric Chalcone Synthase Genes into Petunia Results in Reversible Co–Suppression of Homlogous Genes *in trans*, 1990, *The Plant Cell*, pp. 279–289, vol. 2.

Potrykus, Gene Transfer to Plants: Assessment of Published Approaches and Results, *Annu. Rev. Plant Physiol. Plant Mol. Biol.*, 1991, pp. 205–225, vol. 42.

Salmenkallio–Marttila et al., Transgenic Barley (*Hordeum vulgare* L.) by Electroporation of Protoplasts, *Plant Cell Rep.*, 1995, pp. 301–305, vol. 15.

Torbert et al., Use of Paromomycin as a Selective Agent for Oat Transformation, *Plant Cell Reports*, pp. 635–640, vol. 14.

Thompson et al., Characterization of the Herbicide–Resistance Gene Bar from *Streptomyces Hygroscopcus, EMBO J.*, 1987, pp. 2519–2523, vol. 6.

Wan et al., Generation of Large Numbers of Independently Transformed Fertile Barley Plants, *Plant Physiol.*, pp. 37–48, vol. 104.

Wan et al., Biolistic Transformation of Microspore–Derived and Immature Zygotic Embryos and REgeneration of Fertile Transgenic Barley Plants, In: *Gene Transfer to Plants*, eds. Potrykus an Spangenberg, Springer Verlag, 1994, pp. 139–146.

Wann et al., Type I Callus as a Bombardment Target for Generating Fertile Transgenic Maize (*Zea mays* L.), *Planta*, 1995, pp. 7–14, vol. 196.

Zaghmout and Torello, Plant Regeneration from Callus and Protoplasts of Perennial Ryegras (*Lolium perenne* L.), *J. Plant Physiol.*, 1992, pp. 101–105, vol. 140.

Zhang et al., Production of Multiple Shoots from Shoot Apical Meristems of Oat (*Avena sativa* L.), *J. Plant Physiol.*, 1996, pp. 667–671, vol. 148.

Zhong et al., Plant Regeneration Via Somatic Embryogenesis in Creeping Bentgrass (*Agrostis plaustris* Huds.), *Plant Cell Rep.*, 1991, pp. 453–456, vol. 10.

Zhong et al., *In–Vitro* Morphogeesis of Corn (*Zea mays* L.), *Planta*, 1992, pp. 483–489, vol. 187.

Zhong et al., The Competence of Maize Shoot Meristems for Ingerative Transformation and Inherited Expression of Transgenes, *Plant Physiol.*, 1996, pp. 1097–1107, vol. 110.

METHOD FOR PREPARING BARLEY GREEN REGENERATIVE TISSUE

CROSS-REFERENCE TO RELATED APPLICATION

This application is a divisional of U.S. application Ser. No. 08/845,939, filed Apr. 29, 1997, now U.S. Pat. No. 6,235,529 which is hereby incorporated herein in its entirety by reference.

BACKGROUND OF THE INVENTION

This invention relates to compositions and methods for the in vitro culture, transformation, and regeneration of plants.

Genetic improvement of various crop species by genetic engineering has sometimes been hindered because techniques for in vitro culture, transformation, and regeneration of model cultivars are less effective with recalcitrant commercial cultivars.

Barley (Hordeum vulgare L.) is one of the world's most important cereal crops, closely following wheat, rice, and maize in total production. Barley is used worldwide for feed, food, and malting purposes.

The ability to genetically engineer barley to improve its performance and pest-resistance or to enhance alternative uses is of great importance. The practical utility of stable transformation technologies is largely dependent on the availability of efficient methods for generating large numbers of fertile green plants from tissue culture materials. Procedures have been described for generating highly embryogenic barley callus and regenerating green plants (Dale and Dambrogio, 1979; Handel et al., 1985; Thomas and Scott, 1985; Goldenstein and Kronstadt, 1986; Lürz and Lörz, 1987; Wan and Lemaux, 1994; Hagio et al., 1995; Rahleen, 1996). However, presently available procedures for producing embryogenic callus and regenerating green plants have been of limited utility when used in transformation procedures for commercially important barley genotypes. These procedures have been hampered by a gradual loss of the embryogenic capacity and regenerability of callus tissue and an increase in albino (chlorophyll-deficient) plants during the prolonged periods needed to select transformed tissue. For example, of the independently transformed callus lines generated by one transformation procedure for the barley genotype Golden Promise, only 51% of transformed lines give rise to green plants and some of these lines regenerated only a small number of green plants (Wan and Lemaux, 1994; Lemaux et al., 1996). When the same procedure was applied to the commercial barley genotypes Moravian III and Galena, none of the resulting transformed lines gave rise to green plants.

There is a need, therefore, for efficient methods for transformation and regeneration that can be used with a wide variety of barley genotypes, including commercially important genotypes.

SUMMARY OF THE INVENTION

We have developed improved methods and compositions for plant transformation and regeneration. The examples below detail the application of these methods and compositions to various barley genotypes, including commercially important genotypes that have proven difficult or impossible to transform and regenerate by previously available methods. These improved methods, when applied to barley, result in a significantly higher regeneration frequency, reduce somaclonal variation, and improve the incidence of fertile, green transformed plants. The methods of the present invention are not limited to barley, however, but can be used for transformation and regeneration of other plant species.

One aspect of the present invention encompasses methods for producing a transformed plant that include an intermediate incubation step that improves the frequency with which transformed plants are obtained from independent transformation events. More specifically, such methods comprise the steps of:

(1) transforming a cell of a target plant tissue (e.g., immature embryo, callus, microspore-derived embryo, etc.) to produce a transformed cell;

(2) culturing the transformed cell on a callus-induction medium (CIM) that includes an auxin to promote proliferation of the transformed cell and formation of a transformed callus, i.e., a callus arising from the initial transformation event (in some embodiments, the CIM also contains a low level of a cytokinin and a high level of copper);

(3) culturing the transformed callus on an intermediate-incubation medium (IIM) that includes an auxin and a cytokinin to promote continued proliferation of cells arising from the initial transformation event and formation of a regenerative structure, i.e., a multicellular structure that is competent to regenerate; and (4) culturing the regenerative structure on a regeneration medium (RM; i.e., shooting and/or rooting medium) to produce a transformed plant.

Selection for transformed cells can begin immediately after introduction of DNA into a cell. Alternatively, selection can begin later, e.g., during callus induction in order to provide sufficient time for initial cell proliferation in the absence of the selective agent. Selection is generally maintained during the intermediate incubation step and, depending on the selective agent, can also be maintained during the regeneration step.

Another aspect of the present invention encompasses optimized plant culture media and the use of such media for plant cell and tissue culture. Such optimized media include phytohormones and copper (e.g., cupric sulfate), which improve callus quality during initiation, promote the regenerability of the tissue, and reduce the incidence of albinism during the period of callus maintenance and regeneration. The media also includes conventional plant nutrients and can also include a carbon source such as maltose (which is better than sucrose for initiation of some species, including barley, wheat, and rice).

In preferred embodiments, the CIM includes an auxin (e.g., 2,4-dichlorophenoxyacetic acid or dicamba), for example at a concentration of about 0.1 mg/L to about. 5.0 mg/L, preferably about 1.0 mg/L to about 2.5 mg/L. The CIM can also include a cytokinin (e.g., 6-benzylaminopurine, zeatin, and kinetin), e.g., at a concentration of about 0.01 mg/L to about 0.5 mg/L for initial callus induction and about 0.1 mg/L to about 2.0 mg/L for maintenance of callus and green tissues.

In preferred embodiments, the IIM contains an auxin, e.g., at a concentration of about 0.1 mg/L to about 5.0 mg/L, preferably about 0.5 mg/L to about 2.5 mg/L, and a cytokinin, e.g., at a concentration of about 0.1 mg/L to about 5.0 mg/L, preferably about 0.1 mg/L to about 2.0 mg/L.

The CIM and IIM also preferably include copper, e.g., a concentration of about 0.1 $\mu$M to about 50 $\mu$M.

Another aspect of the present invention encompasses the use of dim light conditions during early phases of selection.

Dim light conditions allow callus to become green and reduce the incidence of regeneration of fertile green plants, and may improve the regenerability of the callus tissue. Dim light conditions also permit one to screen for green portions of the callus (for barley, for example; yellow-green portions for wheat), which are more likely to be regenerable. Green callus is useful as a target plant tissue for transformation, e.g., by microprojectile bombardment or infection by Agrobacterium. Callus grown in dim light on a CIM develops or maintains regenerative structures and can be maintained in this state for at least ten months for Golden Promise, Galena, and Harrington, and at least four to six months for Morex, for example.

Another aspect of the present invention is the use of microprojectile bombardment for plant transformation, wherein the bombardment is performed below 1300 psi, e.g. at 450–900 psi. Lowering the rupture pressure and -hence the speed of the microprojectiles lessens damage to the target tissue and results in less stress to the transformed cells.

Another aspect of the present invention encompasses transformed plants and plant culture media as described herein.

The foregoing and other aspects of the invention will become more apparent from the following detailed description.

DETAILED DESCRIPTION OF THE PREFERRED EMBODIMENTS

Figure 1A:
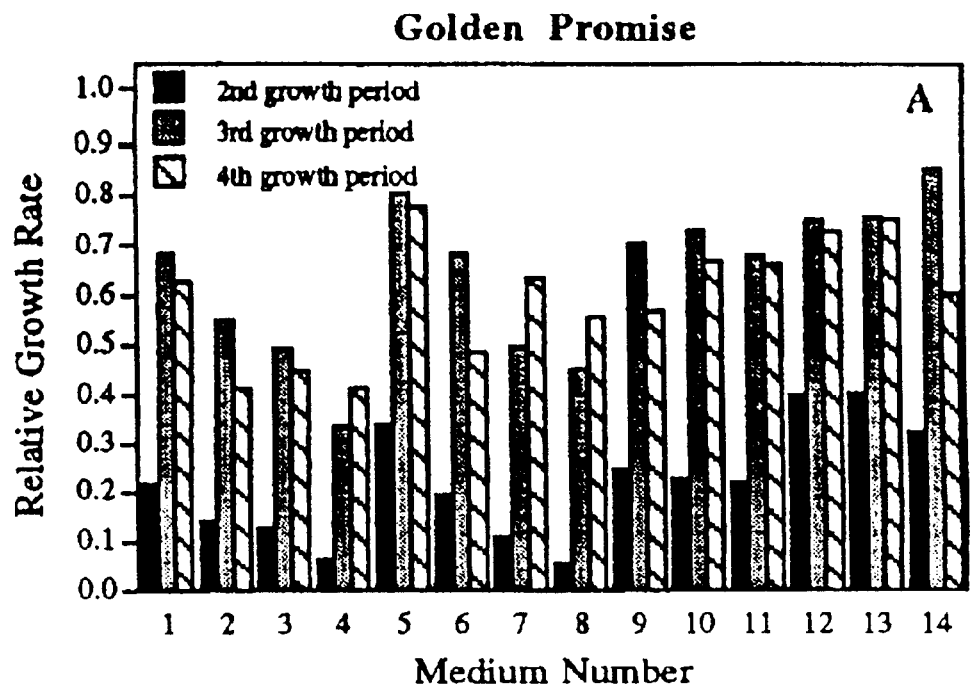
FIG. 1A shows the relative growth rate (g/g fresh weight/day) of callus of the barley genotype Golden Promise grown on fourteen different media. (The auxin and cytokinin concentrations of the media are given in Table 1.)

We have developed improved methods for plant transformation and regeneration and compositions useful for such methods. Although these methods are generally applicable to barley varieties, including recalcitrant genotypes, they are also applicable to other plant species as well.

Definitions and Methods

Unless otherwise noted, terms are to be understood according to conventional usage by those of ordinary skill in the relevant art. In addition to the definitions of terms provided below, definitions of common terms in molecular biology may also be found in Rieger et al., 1991; and Lewin, 1994.

Plant Transformation and Recreneration

"Transformed"; "Transgenic". A cell, tissue, organ, or organism into which a foreign nucleic acid, such as a recombinant vector, has been introduced is considered "transformed" or "transgenic," as is progeny thereof in which the foreign nucleic acid is present.

"Foreign" nucleic acids are nucleic acids that would not normally be present in the host cell, particularly nucleic acids that have been modified by recombinant DNA techniques. The term "foreign" nucleic acids also includes host genes that are placed under the control of a new promoter or terminator sequence, for example, by conventional techniques.

Transformation by particle bombardment. Particle bombardment has been employed for transformation of a number of plant species, including barley (see, e.g., Wan and Lemaux, 1994, and BioRad Technical Bulletin 2007) and corn (see, e.g., Gordon-Kamm et al., 1990). Successful transformation by particle bombardment requires that the target cells are actively dividing, accessible to microprojectiles, culturable in vitro, and totipotent, i.e., capable of regeneration to produce mature fertile plants.

Target tissues for microprojectile bombardment include immature embryos, young embryogenic callus from immature embryos, microspores, microspore-derived embryos, and apical meristem tissue. We have also found that green callus tissues are useful targets for bombardment, as discussed below.

Previously, bombardment of barley tissue such as immature zygotic embryos or young callus tissue was generally carried out at 1100 psi. We have found that a rupture pressure under 1100 psi, preferably less than 1000 psi, more preferably about 600 to 900 psi, resulted in a higher callus-induction frequency and a higher frequency of regenerative structures in Galena, for example, possibly due to reduced damage to the target tissue (although Golden Promise was unaffected in its frequency).

Green Tissues as a Target for Particle Bombardment.

Barley callus tissue that is not exposed to light is moved through selection as rapidly as possible, since longer culture times result in lower regenerability and a higher incidence of albinism (Lemaux et al., 1996). We have discovered that green barley callus tissue can be maintained for more than 10 months (e.g., Golden Promise, Galena, Harrington, and Salome) on an IIM (discussed in detail below) and can subsequently regenerate at high frequency when transferred to a regeneration medium. The use of green tissues as a target for transformation by microprojectile bombardment permits long-term culture of barley, reducing the need to maintain high-quality donor plants throughout the year. It may also reduce the need to backcross barley transformants, since the green callus tissue is more highly differentiated than tissue that has not been exposed to light and may have a lower frequency of induced mutation and be less likely to exhibit somaclonal variation. Moreover, the incidence of albinism is significantly reduced compared to dark-grown tissue.

Other Plant Transformation Methods.

Any conventional method may be employed to transform plants, i.e., to introduce foreign DNA into a plant cell. The generation of stable transformants and fertile transgenic plants has been achieved, for example, in a wide variety of dicotyledonous plants and in such cereals as rice, maize, wheat, and oat by a variety of methods.

In addition to particle bombardment, conventional methods for plant cell transformation include, but are not limited to: (1) Agrobacterium-mediated transformation, (2) microinjection, (3) polyethylene glycol (PEG) procedures, (4) liposome-mediated DNA uptake, (5) electroporation, and (6) vortexing with silica fibers.

Regeneration of Transformed Plant Cells.

Transformed plant tissues are cultured on a regeneration medium to cause differentiation of the tissue to produce a fertile transgenic plant.

It is preferable that callus-induction and plant-regeneration be accomplished in three stages, each involving transformed cells or tissues on a medium supporting the biological events desired at each stage: callus induction, intermediate incubation, and regeneration.

"Callus-induction medium" (CIM) preferably promotes a fast growth rate without allowing substantial differentiation of the plant tissue into organized structures. A transformed cell arising from introduction of foreign DNA into a cell is incubated on CIM for a time sufficient for the cell to proliferate to form sufficient callus tissue to ensure that a sufficient number of progeny cells are produced from a single transformed cell to form numerous somatic embryos that will give rise to numerous transformed plants when regenerated. For that reason, CIM preferably includes an auxin (e.g., about 0.5 mg/L to about 5.0 mg/L of 2,4-dichlorophepoxyacetic acid [2,4-D] or dicamba) to promote rapid cell division. Cytokinin levels are preferably kept low for most genotypes for initial callus induction, particularly for recalcitrant genotypes (such as the barley genotypes Galena, Morex, or Harrington), because high cytokinin levels decrease the initial growth rate of the callus (high cytokinins also interfere with selection using bialaphos, although not when hygromycin or G418 is used). However, a cytokinin improves callus quality and regenerability and may reduce the incidence of albinism (i.e., induce the growth of more green regenerative tissues). Therefore, low levels of a cytokinin may be included in the CIM, -e.g., 6-benzylaminopurine [BAP], zeatin, kinetin, etc., preferably BAP or kinetin, at levels of about 0.01 mg/L to about 1.0 mg/L for initial callus induction, about 0.1 mg/L to about 2.0 mg/L for callus maintenance. The optimal level of cytokinin depends on the genotype. CIM also preferably contains copper (about 0.1 $\mu$M to about 50 $\mu$M).

Callus tissue is divided into smaller pieces (e.g., for barley, pieces of about 3 to 5 mm are preferred) and subcultured, i.e., transferred to fresh medium, at regular intervals to promote optimal growth rates. For barley, the tissue is subcultured at an interval of about 2–3 weeks if a low level (about 0.01 mg/L) of BAP is used and about 3–4 weeks if a higher level of BAP is used (about 0.1 mg/L to about 0.5 mg/L).

Preferably, the tissues are initially cultured without selection. In Example 4 below, for example, selection was not applied immediately after bombardment in order to allow for the proliferation of transformed cells in the absence of dead or dying cells resulting from wounding or selection (about 1–2 weeks if immature embryos are used as a target source and 3–4 weeks if green tissues are used). After this period, selection is applied to select for transformed cells. Selection can be accomplished by adding a selection agent to the culture medium for which the foreign DNA in transformed cells confers resistance (assuming that a selectable marker is included on the foreign DNA). Putative transformants are identified by their faster growth on the selective medium relative to nontransformed-tissue. Screenable markers (e.g., green fluorescent protein) can also be used to identify transformed tissue.

Transformed tissues preferably are maintained initially on CIM in the dark (e.g., for about 3–4 weeks on CIM as in Example 3), then cultured under dim light conditions (for barley, approximately 10 to 30 $\mu$E m$^{-2}$s$^{-1}$). The use of dim light conditions has been found to reduce or eliminate the regeneration of albino barley plants (as observed in Wan and Lemaux, 1994).

For barley, embryogenic structures appear as fast-growing shiny, slightly brown-colored, nodular, compact structures. Under dim light these structures often appear as multiple meristem-like structures with small green shoots. By contrast, nontransformed tissues generally lack nodular structures and appear watery, loose and friable, or round and slow-growing. After embryogenic structures are observed in the putatively transformed tissue, the tissue is transferred to an "intermediate-incubation medium" (IIM). Incubation of the tissue on an IIM permits continued rapid growth, albeit at a slower pace than CIM. Incubation on an IIM improves the likelihood of the formation of regenerative structures and competence for regeneration by promoting the transition of the developmental pathway of a plant tissue from an embryogenic route to an organogenic route.

IIM suppresses the extension of shoots and can be used to maintain and proliferate green sectors or green vegetative structures for long periods of time until they have reached sizes and numbers appropriate for regeneration (with barley, green regenerative tissues of certain genotypes can be maintained for more than ten months on DBC2 medium, (the composition of which is given below), at least about eight months for Golden Promise, Galena and Harrington, and at least about four to six months for Morex, for example).

IIM preferably includes an auxin (about 0.5 mg/L to about 2.5 mg/L 2,4-D or dicamba) for continued cell proliferation. IIM preferably also includes high cytokinin concentrations (e.g., about 0.1 mg/L to about 2.0 mg/L BAP) and high copper concentrations (e.g., about 0.1 $\mu$M to about 50 $\mu$M, preferably about 5 to about 30 $\mu$M. The higher cytokinin concentration reduces the rate of cell division but promotes progress to competence for regeneration and might reduce the incidence of albinism.

Copper concentrations in the IIM are preferably at least as high as levels in MS medium (0.1 $\mu$M, Murashige and Skoog, 1962), preferably at least 5-fold higher, more preferably at least 10-fold, more preferably at least 20-fold, most preferably at least 50-fold higher optimal copper levels vary with the genotype and species. Higher copper levels promote improved callus quality and regenerability without reducing callus-induction frequency or the initial callus growth rate. High copper levels may have less effect or no effect when included in regeneration medium.

The term "copper" is used herein to include any well-known nutritional source of copper for plant culture media, e.g., cupric sulfate.

The effects of copper and BAP on the regenerability of transformed barley tissues appear to be more than additive, i.e., there appears to be a synergistic effect when the IIM includes both high levels of copper and high levels of BAP.

It is desirable to generate large numbers of plants from a single independently transformed callus line due to transcriptional and translational inactivation phenomena and somaclonal variation. In commercial cereals, for example, the number of transformants resulting from conventional transformation protocols has proven limiting in efforts to employ genetic engineering to achieve crop improvement. Incubation of transformed callus on an IIM prior to transfer to a regeneration medium maximizes the frequency at which individual transformation events give rise to transformed plant lines. The use of an intermediate incubation step increased the regeneration frequency for Golden Promise up to at least 65 percent and resulted in an increase in the number of transformed plants produced per callus piece of up to 11.4-fold.

Transformed tissue can be transferred from IIM to rooting or regeneration medium when embryogenic structures are observed (for barley, after about 3 or-4 rounds of subculturing or after approximately 9–16 weeks post-bombardment depending on the genotype and growth rate). The selection period should be longer when BAP is used in the CIM and IIM (about 3–4 months for Golden Promise and about 4–6 months for Galena).

"Regeneration medium" (RM) promotes differentiation of totipotent plant tissues into shoots, roots, and other organized structures and eventually into plantlets that can be transferred to soil. It is often preferable to employ a shooting medium to promote shoot regeneration from embryogenic structures and a separate rooting medium to promote root formation. Depending upon the genotype, different levels of an auxin (e.g., 2,4-D) and a cytokinin (e.g., BAP) provide optimal results. For many barley genotypes RM contains BAP (about 0–8 mg/L) without auxin. However regeneration of Morex is improved by addition of auxin (2,4-D) to the RM. Conventional shooting and rooting media are considered regeneration media.

Any well-known regeneration medium may be used for the practice of the methods of the present invention. For barley, FHG medium (Hunter, 1988, and described in Kasha et al., 1990) is preferred.

As used herein, "plant culture medium" refers to any medium used in the art for supporting viability and growth of a plant cell or tissue, or for growth of whole plant specimens. Such media commonly include defined components including, but not limited to, macronutrient compounds providing nutritional sources of nitrogen, phosphorus, potassium, sulfur, calcium, magnesium, and iron; micronutrients, such as boron, molybdenum, manganese, cobalt, zinc, copper, chlorine, and iodine; carbohydrates (preferably maltose for barley, although sucrose may be better for some species); vitamins; phytohormones; selection agents (for transformed cells or tissues, e.g., antibiotics or herbicides); and gelling agents (e.g., agar, Bactoagar, agarose, Phytagel, Gelrite, etc.); and may include undefined components, including, but not limited to: coconut milk, casein hydrolysate, yeast extract, and activated charcoal. The medium may be either solid or liquid, although solid medium is preferred.

Any conventional plant culture medium can be used as a basis for the formulation of CIM, IIM, and RM when appropriately supplemented. In addition to the media discussed in the Examples below (e.g., MS medium and FHG medium), a number of such basal plant culture media are commercially available from Sigma (St. Louis, Mo.) and other vendors in a dry (powdered) form for reconstitution with water, for example.

Any well-known auxin or cytokinin may be used in the practice of the invention. Auxins include, but are not limited to, 2,4-D, dicamba, indoleacetic acid, and naphthalenacetic acid. Cytokinins include, but are not limited to, BAP, kinetin, zeatin, zeatin riboside, and $N^6$-(2-isopentenyl) adenine (2iP). A particular genotype or species may respond optimally to a specific phytohormone, as noted in the Examples below.

Albinism. Albinism is a common problem in barley tissue culture (Kott and Kasha, 1984; Kasha et al., 1990; Jähne et al., 1991). Albinism is influenced by a number of factors, including genetic background (Foroughi-Wehr et al, 1982), physiological state of the donor plants (Goldenstein and Kronstadt, 1986), exposure to bialaphos (Wan and Lemaux, 1994), length of time in culture (Bregitzer et al., 1995), and culture conditions (Kao et al., 1991).

Wan and Lemaux (1994) reported that, of 91 transgenic callus lines generated by particle bombardment of various target tissues, 36 lines yielded green plants and 41 yielded only albino plants. Lemaux et al. (1996) reported that, of 73 transgenic callus lines generated by particle bombardment, 37 lines yielded green plants and 20 yielded only albino plants.

The improved methods discussed herein significantly reduce the incidence of albinism below levels reported previously. Preferably, the percentage of putative transformation events that regenerate to produce green transformed barley plants (and not albino plants), i.e., the number of transformation events yielding green plants divided by the total number of transformation events yielding green and albino plants×100 percent, is at least about 60 percent, preferably at least about 75 percent, and most preferably at least about 90 percent.

The methods described herein also reduce problems associated with induced heritable mutation and somaclonal variation that can result from long-term maintenance of plant tissue in culture.

"Plant". The term "plant" encompasses transformed plants, progeny of such transformed plants, and parts of plants, including reproductive units of a plant, fruit, flowers, seeds, etc. The transformation methods and compositions of the present invention, is applicable to various barley genotypes (e.g., Morex, Harrington, Crystal, Stander, Moravian III, Galena, Salome, Steptoe, Klages, Baronesse, etc.) as well as to other species of monocotyledonous plants (e.g., wheat, corn, rice, etc.), or dicotyledonous plants (e.g., tomato, potato, soybean; cotton, tobacco, etc.).

A "reproductive unit" of a plant is any totipotent part or tissue of the plant from which one can obtain progeny of the plant, including, for example, seeds, cuttings, tubers, buds, bulbs, somatic embryos, microspores, cultured cells (e.g., callus or suspension cultures), etc.

Nucleic Acids

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA. The term also embraces recombinant nucleic acids and chemically synthesized nucleic acids.

"Operably Linked". Nucleic acids can be expressed in plants or plant cells under the control of an operably linked promoter that is capable of driving expression in a cell of a particular plant. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary, to join two protein coding regions to produce a hybrid protein.

"Recombinant". A "recombinant" nucleic acid is made by an artificial combination of two otherwise separated segments of sequence, e.g., by chemical synthesis or by the manipulation of isolated segments of nucleic acids by conventional genetic engineering techniques.

"Vectors, Transformation, Host cells". Nucleic acids can be incorporated into recombinant nucleic-acid constructs, typically DNA constructs, capable of being introduced into and replicating in a host cell. Such a construct preferably is a vector that includes sequences that are capable of transcription and translation of a polypeptide-encoding sequence in a given host cell (and may include a replication system, although direct DNA introduction methods conventionally used for monocot transformation do not require this).

For the practice of the present invention, conventional compositions and methods for preparing, and using vectors and host cells are employed, as discussed, inter alia, in Sambrook et. al., 1989, or Ausubel et al.,. 1992.

A number of vectors suitable for stable transformation of plant cells or for the establishment of transgenic plants have been described in, e.g., Pouwels et al., 1987, Weissbach and Weissbach, 1989, and Gelvin et al., 1990. Typically, plant expression vectors include, for example, one or more cloned plant genes under the transcriptional control of 5' and 31 regulatory sequences and a dominant selectable marker. Such plant expression vectors also can contain a promoter regulatory region (e.g., a regulatory region controlling inducible or constitutive, environmentally-or developmentally-regulated, or cell- or tissue-, specific expression), a transcription initiation start site, a ribosome binding site, an RNA processing signal, a transcription termination site, and/or a polyadenylation signal.

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters); light (e.g., pea rbcS-3A or maize rbcS promoters or chlorphyll a/b-binding protein promoter); phytohormones, such as abscisic acid; wounding (e.g., wunI); anaerobiosis (e.g., Adh), and chemicals such as methyl jasmonate, salicylic acid, or safeners. It may also be advantageous to employ well-known organ-specific promoters such as endosperm-, embryo-, root-, phloem-, or trichome-specific promoters, for example.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for plant cell transformation, including color markers such as genes encoding β-glucuronidase (gus) or anthocyanin production, or fluorescent markers such as genes encoding luciferase or green fluorescence protein (GFP).

The invention will be better understood by reference to the following Examples, which are intended to merely illustrate the best mode now known for practicing the invention. The scope of the invention is not to be considered limited thereto.

EXAMPLES

Example 1

Improvement of Callus Quality and Regenerability in Barley Genotypes Golden Promise and Galena Materials and Methods Plant Material. Donor plants for immature embryos were grown in soil under controlled conditions in growth chambers as described (Wan and Lemaux, 1994; Lemaux et al., 1996).

As noted in other Examples below, plants were grown in a greenhouse (immature embryos grown in the growth chambers are preferred for green tissue culture). The greenhouse had supplementary lighting providing a 14-h photoperiod with temperatures of 15 to 18° C. Supplemental 1000-watt metal-halide lights were engaged when the light level in the greenhouse was less than 1000 $\mu$E m$^{-2}$ s$^{-1}$. Roof shades covered the roof when outside light levels rose above 7000 $\mu$E m$^{-2}$ s$^{-1}$.

Spring cultivars of barley (*Hordeum vulgare L.*) Golden Promise and Galena were used as donor plants. Galena seed was obtained from B. Treat, Coors Brewing Company, Golden, CO. Golden Promise seed was obtained from P. Bregitzer, USDA-ARS Small Grains Germplasm Center, Aberdeen, Id.

"Media". Callus-induction medium (CIM) is MS medium (Murashige and Skoog, 1962) supplemented with 30 g/L maltose, 1.0 mg/L thiamine-HCl, 0.25 g/L myo-inositol, 1.0 g/L casein hydrolysate, 0.69 g/L proline, and solidified with 3.5 g/L Phytagel (Sigma, St. Louis, Mo.). CIM was supplemented with fourteen different combinations of two auxins (dicamba and 2,4-dichlorophenoxyacetic acid [2,4-D]) and two cytokinins (6-benzylaminopurine [BAP] and zeatin) as shown in Table 1, and the supplemented medium was tested for callus induction, callus quality, growth rate, and regenerability.

Regeneration medium (RM) is FHG medium (Hunter, 1988; Kasha et al., 1990), a modified MS medium with lower $NH_4NO_3$ and high glutamine, supplemented with 1 mg/L BAP and solidified with 3.0 g/L Phytagel. The composition of FHG medium is 165 mg/L $NH_4NO_3$, 1.90 g/L $KNO_3$, 440 mg/L $CaCl_2.2H_2O$, 370 mg/L $MgSO_4.7H_2O$, 170 mg/L $KH_2PO_4$, 16.9 mg/L $MnSO_4.H_2O$, 8.6 mg/L $ZnSO_4.7H_2O$, 6.2 mg/L $H_3BO_3$, 0.83 mg/L KI, 0.25 mg/L $Na_2MoO_4.2H_2O$, 25 $\mu$g/L $CuSO_4.5H_2O$, 25 $\mu$g/L $CoCl_2.6H_2O$, 0.4 mg/L thiamine-HCl, 100 mg/L inositol, 730 mg/L glutamine, 62 g/L maltose, 27.8 mg/L $FeSO_4.7H_2O$, 33.5 mg/L $Na_2EDTA$, 1.0 mg/L BAP, 3 g/L Phytagel, pH 5.6.

"Callus induction and scoring". Immature embryos (about 1.5–2.5 mm in size) were taken from spikes approximately three months in age that were surface-sterilized in 20% (v/v) bleach (5.25% sodium hypochlorite) for 7 min, washed 5 min with sterile water three times, bisected longitudinally, and placed on CIM. Ten half-embryos were tested on CIM supplemented with each of the fourteen phytohormone combinations; each treatment had three replicates. (Whole embryos can also be used.) Callus-induction frequency was measured by counting numbers of half embryos undergoing callus induction under a light microscope 2 to 3 weeks after initial culturing.

Two embryo sizes were tested: small (0.5–1.5 mm) and large (1.5–2.0 mm). Golden Promise is good in callus induction with both small- and large-sized embryos, but callus induction is very poor with small-sized embryos of Galena.

"Callus growth rate". For determining callus growth rates, ten half embryos were placed scutellum-side down on a Petri dish containing each medium; each treatment had three replicates. Every 2 to 3 weeks, callus pieces were weighed and the growth rate was determined by weighing the plate containing the callus pieces before transfer (WI) and after transfer of all tissue ($W_2$). The relative growth of the callus was calculated as the change in weight (W) of the callus ($W=W_1-W_2$), divided by the weight of the tissues originally plated ($W_1$) and the number of culture days (g/g fresh weight/day). From the third transfer, three of the highest-quality pieces, rather than all calli from each embryo, were transferred onto fresh medium. All calli that were not transferred were removed from the plate to obtain $W_2$.

"Callus quality". Callus quality (morphology and color) was assessed microscopically 2 to 3 weeks after initial callus induction. For morphology, a score of ++++ (highest quality) was given to shiny, compact, nodular callus; a score of + (lowest quality) was given to soft, friable callus. Color was judged from slightly brown-colored callus (++++) to white (+).

"Regeneration". To test regeneration, ten pieces of highest-quality callus (8 to 11 mg per piece) from each treatment were transferred to RM in three replicates at varying times during the culture period. Dishes were placed at 24±1° C. under fluorescent lights (45 to 55 $\mu$E m$^{-2}$ s$^{-1}$, 16 h light/8 h dark). The number of shoots per callus piece was counted about 22–25 days after transfer. (One or more leaves arising from the same base of green tissue was considered as one shoot.)

Results

Transduction frequency, relative growth rate, and qualitative appearance of callus. To examine the effects of different concentrations and types of auxins and cytokinins on callus-induction frequency, quality, and relative growth rate, 14 different media were tested (Table 1, left two columns). On most media, callus-induction frequencies were not statistically different for Golden Promise and Galena; dicamba and 2,4-D alone and dicamba with zeatin at all concentrations resulted in nearly 100% induction frequencies for both genotypes. Golden Promise had a significantly higher callus-induction frequency than Galena on 3 of the 14 media tested: dicamba+0.1 mg/L BAP, dicamba+0.5 mg/L BAP, and 2,4-D+0.5 mg/L BAP. Galena had a significantly higher callus-induction frequency than Golden Promise on only one medium, 2,4-D+0.01 mg/L zeatin. With Galena, higher levels of BAP in combination with 2,4-D, or, more significantly, in combination with dicamba, led to lower callus-induction frequencies.

Callus induction from Golden Promise embryos occurred over most of the surface area of the scutellum, while Galena callus was produced from a much smaller area of the embryo.

Color assessments of the two genotypes on the same medium were identical. However, in general, callus morphology of Golden Promise was better than that of Galena on nearly all media tested (Table 1). Certain trends in morphology were seen for both genotypes. First, culturing on medium containing BAP in combination with either 2,4-D or dicamba produced a better callus morphology than culturing on medium containing zeatin with either 2,4-D-or dicamba (Table 1). Second, callus color in both genotypes was dramatically affected by the type of cytokinin (Table 1). Increasing BAP levels (with either auxin) led to the formation of more slightly brown-colored callus, whereas zeatin at all levels (with either auxin) led to the formation of poor quality, white callus (Table 1). Third, medium containing higher concentrations of BAP (0.1 to 0.5 mg/L with 2,4-D) appeared to support the production of higher quality callus (morphology and color) than did the lower concentration of BAP (0.01 mg/L) with both genotypes (Table 1).

Figure 1B:
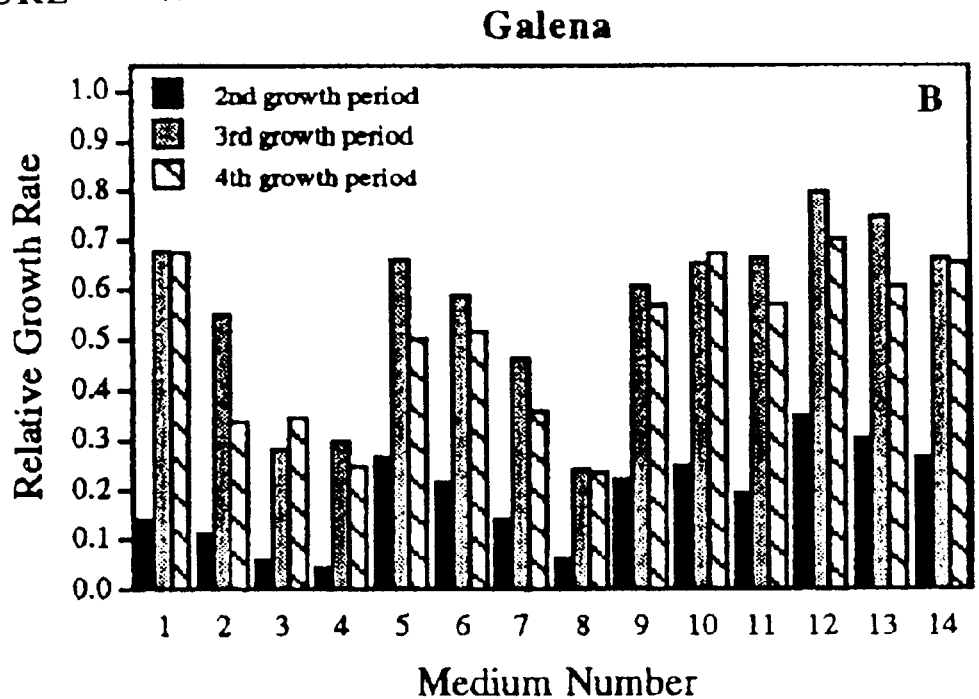
FIG. 1B shows the relative growth rate (g/g fresh weight/day) of callus of the barley genotype Galena (B) grown on fourteen different media. (The auxin and cytokinin concentrations of the media are given in Table 1.)

In the first growth period, determination of the growth rate was complicated by the rapid increase in fresh weight of the starting material due to imbibition of the embryo. By the third transfer, the relative growth rate increased rapidly, reaching its maximum (FIG. 1). Growth rates dropped significantly after the fourth growth period. For both genotypes, growth rates on media containing BAP were generally slower than in the absence of BAP or in the presence of zeatin. Golden Promise appeared to grow faster than Galena on media containing dicamba plus BAP and 2,4-D+/−BAP. Both genotypes grew faster on medium containing 2,4-D plus BAP than on medium containing dicamba plus BAP (except for Galena at 0.5 mg/L BAP). There appeared to be little variation between genotypes in growth rate on medium containing 2,4-D or dicamba in combination with zeatin. The use of low concentrations of zeatin (0.01 or 0.1 mg/L) in combination with dicamba or 2,4-D did not appear to inhibit the callus growth rate of Golden Promise relative to growth on dicamba or 2,4-D alone, and the combination of low concentrations of zeatin with 2,4-D seemed to increase the callus growth rate of Galena up to the fourth growth period relative to 2,4-D alone (FIG. 1).

Plant regeneration. Calli of Golden Promise and Galena grown on the fourteen different media were tested for their ability to regenerate plants. In general, Golden Promise produced a higher number of green calli (NC) and green shoots (NS) per 10 initial callus pieces than did Galena at most time points on most media (compare Tables 2 and 3). In addition, Galena callus appeared to lose regenerability at a faster rate than Golden Promise except on callus-induction media containing BAP in combination with 2,4-D, in which case Galena responded more favorably than Golden Promise at all levels of BAP.

For Golden Promise (Table 2), through the fifth transfer all treatments produced comparable numbers of green calli, while 2,4-D plus 0.01 and 0.5 mg/L BAP appeared to yield the highest numbers of shoots. In most cases the number of shoots and green calli decreased dramatically after either the fifth or seventh transfers. One of the most dramatic losses was at the seventh transfer with the use of dicamba alone, where no green calli were observed. Few media supported the regeneration of plants at the ninth transfer. Only dicamba and 2,4-D plus 0.1 mg/L BAP and 2,4-D plus 0.5 mg/L zeatin supported long-term shoot regenerability in Golden Promise.

For Galena (Table 3), on medium-containing either (1) dicamba or 2,4-D with zeatin or (2) dicamba in combination with BAP, the ability to generate green shoots was lost more rapidly than with Golden Promise. The only media supporting long-term maintenance of greening and regeneration of plants (7th transfer and beyond) was 2,4-D plus BAP at all levels. Media containing 0.1 mg/L BAP appeared optimal at the latest time point and supported a faster callus growth rate than dicamba plus a comparable level of BAP (FIG. 1).

For both genotypes, medium containing BAP in combination with 2,4-D (and to a lesser extent dicamba) supported the development of multiple shoots from the shiny, compact callus tissues (Tables 1–3), while few or no shoots developed on a medium containing 2,4-D alone.

Discussion

In these experiments, medium composition and phytohormone types and levels were important factors in determining tissue culture responses. Certain generalizations can be made regarding the effects of different cytokinins on the properties of proliferated callus. Although medium containing zeatin appeared to support faster growth rates, medium containing zeatin (plus 2,4-D or dicamba) also produced lower quality (soft, light-colored) callus compared to medium containing BAP (plus 2,4-D or dicamba) (Table 1).

The detrimental effects of zeatin can also be seen by comparing the regenerative potential of calli from both genotypes grown on medium including either BAP or zeatin. Calli grown on medium containing zeatin (from 0.01 to 0.5 mg/L) were less regenerative than calli grown on medium containing BAP and regenerated on the same RM (Tables 2 and 3). This finding is in contrast to that of Lürz and Lörz, (*Theor. Appl. Genet.*, 75:16–25, 1987), who showed that, in combination with IAA, zeatin and zeatin riboside (0.05 mg/L) increased the frequency of regeneration, of somatic.embryos from the barley genotypes Golden Promise and Dissa, while higher levels reduced regeneration. Other cytokinins, such as BAP, kinetin, and 2iP, were shown to cause callus browning and necrosis of somatic embryos. Media containing IAA and zeatin has also been shown to improve regenerablity of immature embryo-derived callus of *Hordeum spontaneum* and *H. bulbosum* (Breimann, *Plant Cell Rep.*, 4:161–163, 1985). The fact that we did not observe a positive effect of zeatin on the tissue culture response of Golden Promise and Galena may result from the particular barley genotypes, the different auxins (dicamba and 2,4-D) we employed, or other modifications in our culturing procedures.

In contrast to zeatin, the addition of BAP to 2,4-D-containing medum decreased the growth of the soft, friable callus and increased the frequency of embryogenic, shiny, compact and slightly brown-colored callus that was more highly regenerative (Table 1). In many cases, calli grown on media containing low concentrations of BAP (0.01 or 0.1 mg/L) in combination with 2,4-D yielded the largest numbers of regenerated shoots for a particular genotype; with Galena, 2,4-D+BAP prolonged the regeneration period for green plants. The auxin 2,4-D is most commonly used for embryogenic callus formation in cereal crops, but the addition of cytokinin to 2,4-D can be significant, depending on plant species and genotypes (reviewed by Bhaskaran and Smith, *Crop Sci.*, 30:1328–1336, 1990). Recently, multiple shoots were differentiated from excised shoot apical meristems in maize (Zhong et al., *Planta*, 187:483–489, 1992) and oat (Zhang et al, *J. Plant Physiol.*, 148:667–671, 1996) cultured on BAP and 2,4-D. This effect of BAP on shoot regeneration is also consistent with previous observations on Kentucky bluegrass (Griffin and Dibble, *Plant Cell Rep.*, 14:721–724, 1995) and creeping bentgrass (Zhong et al., *Plant Cell Rep.*, 10:453–456, 1991), where higher frequencies of shoot regeneration from seed-derived callus were achieved when auxin (dicamba or 2,4-D) and BAP were substituted for auxin alone.

In our study the positive effect of BAP in combination with 2,4-D was also reflected in callus quality (Table 1). Shiny, compact and slightly brown-colored callus produced green plants. Compact, light-colored callus was regenerative but generally produced albino plants. Soft, friable callus was not regenerative. For both Golden Promise and Galena, the addition of BAP (in combination with either 2,4-D or dicamba) decreased the growth of the soft, friable, white callus and increased the proportion of compact, slightly brown-colored regenerative callus relative to no cytokinin or comparable concentrations of zeatin (Table 1).

Golden Promise calli grown on medium containing 0.01 mg/L BAP in combination with 2,4-D regenerated almost the largest (fourth/seventh transfers) or equivalent (fifth) numbers of green shoots relative to the other media (Table 2). Calli grown on medium containing 0.1 mg/L BAP with 2,4-D produced fewer (and shorter) green shoots than media with 0.01 mg/L at all but the third and ninth transfers (Table 2). For Galena, growth on medium containing 2,4-D with 0.1 mg/L of BAP produced callus that yielded the most green plants at all transfer times except the third (Table 3). When calli with small, green, compact shoots were transferred for the second time from medium containing 2,4-D and 0.1 mg/L BAP onto fresh regeneration medium, more tissue containing multiple shoots was seen than when 0.01 mg/L BAP was used. It is possible that the BAP-containing medium caused the callus tissue to proliferate for prolonged periods in a regenerable state.

The negative effects of the length of time in culture on regenerative potential is also documented in this study. On all media, immature embryos of Golden Promise produced fast-growing., embryogenic callus that gave rise to green plants at high frequencies for periods up to two months (fifth transfer) after initial callus induction (Table 1 and 2; FIG. 1). After the fifth transfer, Golden Promise calli began to lose regenerative potential (Table 2). Galena lost regenerability much more rapidly than Golden Promise on all media tested, except for media containing 2,4-D plus BAP (Table 3), with regenerability declining on most media after the fourth transfer. Therefore, longer periods of culturing in the dark led to lower total numbers of regenerated green plants from both Golden Promise and Galena (Tables 2 and 3), with the losses in Galena being more marked.

Culture time also appeared to affect albinism. There was a smaller number of green calli in Galena cultures relative to Golden Promise at later time points (seventh, ninth) on most media (Tables 2 and 3). Some albino plants were produced from Golden Promise at later transfer times. However, when cultured on the same medium for the same length of time, Galena produced larger numbers of albino plants. The propensity of Galena toward albinism is also supported by data collected during regeneration tests of 1-month-old Golden Promise and Galena calli grown on 2,4-D (2.5 mg/L) in combination with BAP (0.1 mg/L). From this material, 70 to 80%; of the GP cells became green under dim light conditions (10 to 20 $\mu E$ $m^{-2}$ $s^{-1}$), whereas less than 20% of the cells from a comparably aged Galena culture had greening potential.

Thus, the length of time in culture and genotypic differences have dramatic effects on albinism and hence on the ability to regenerate green plants.

Embryo size is another important factor affecting callus-induction frequencies.

Optimal embryo size varies with genotype. Using embryo sizes larger than 2.5 mm from both genotypes resulted in low callus-induction frequencies. Galena embryos from 0.5 to 1.2 mm in size had very low callus-induction frequencies (<20%) while Golden Promise embryos of the same size had a frequency of over 90%. The highest callus-induction frequencies with Golden Promise were associated with calli from 0.5 to 2.0 mm in size, while the optimal size for Galena was 1.5 to 2.0 mm. The effect of size on callus-induction frequency is likely due to the effects of the exogenously applied hormones on the developmental cascades that are triggered in a particular sized, immature embryo and the developmental flexibility of the particular genotype.

The frequency of induction, quality, and regenerability of callus in barley are influenced by a variety of factors, such as media composition (Bregitzer, 1992; Dahleen, 1995; Handel et a!, 1985; Lürz and Lörz, 1987), phytohormones (Hagio et al., 1995; Ziauddin and Kasha, 1990; Lürz and L orz, 1987), length of time in culture (Lürz and Lörz, 1987; Bregitzer et a!, 1995), embryo size (Baillie et: al., 1993; Ziauddin and Kasha, 1990; Dale and Dambrogio, 1979), and genotype (Dahleen, 1996; Baillie et a!, 1993; Bregitzer, 1992; Lürz and Lörz, 1987; Goldenstein and Kronstadt, 1986; Handel et al., 1985). We have confirmed and expanded these observations to the transformable barley cultivar Golden Promise and a recalcitrant commercial barley variety, Galena.

Using a previously published transformation protocol that employed a medium containing 2.5 mg/L dicamba and no cytokinin (Wan and Lemaux, 1994), we obtained large numbers of transformed callus lines with Galena, but all lines yielded only albino plants. We have identified optimal combinations and levels of auxin and cytokinin for production of the highest quality, regenerative callus of Golden Promise and Galena during prolonged tissue culture periods. For both genotypes, 2,4-D in combination with BAP (between about 0.01 and about 0.1 mg/L) was found to be optimal for prolonging regenerability and producing the highest numbers of green calli and shoots. These phytohormone conditions can be adjusted for optimal results with other barley genotypes and for other plant species as well.

TABLE 1

Callus-Induction Frequency and Qualitative Appearance of Golden Promise and Galena

| Auxin Conc. (mg/L) | Cytokinin conc. (mg/L) | Callus Induction Frequency (%)[a] | | Callus Morphology[d] | | Callus Color[e] | |
|---|---|---|---|---|---|---|---|
| Dicamba | BAP | GP[b] | GAL[c] | GP | GAL | GP | GAL |
| (1) 2.5 | 0 | 100 ± 0 | 100 ± 0 | +++(+) | + | ++ | + |
| (2) 2.5 | 0.01 | 96.3 ± 5.2 | 92.6 ± 5.2 | +++ | +(+) | ++ | ++ |
| (3) 2.5 | 0.1 | 88.9 ± 0 | 71.3 ± 12.4 | +++ | ++ | ++ | ++ |
| (4) 2.5 | 0.5 | 92.6 ± 5.2 | 54.2 ± 5.9 | +++ | +++ | +++ | +++ |
| 2,4-D | | | | | | | |
| (5) 2.5 | 0 | 92.6 ± 5.2 | 100 ± 0 | +++ | +(+) | ++ | ++ |
| (6) 2.5 | 0.01 | 100 ± 0 | 96.3 ± 5.2 | +++(+) | ++ | +++ | +++ |
| (7) 2.5 | 0.1 | 84.3 ± 6.6 | 84.3 ± 6.6 | ++++ | +++ | ++++ | ++++ |
| (8) 2.5 | 0.5 | 92.6 ± 5.2 | 75.0 ± 0 | ++++ | +++ | ++++ | ++++ |
| Dicamba | Zeatin | | | | | | |
| (9) 2.5 | 0.01 | 100 ± 0 | 96.3 ± 5.2 | ++ | + | + | + |
| (10) 2.5 | 0.1 | 100 ± 0 | 100 ± 0 | +++ | ++ | + | + |
| (11) 2.5 | 0.5 | 100 ± 0 | 100 ± 0 | ++ | + | + | + |
| 2,4-D | | | | | | | |
| (12) 2.5 | 0.01 | 79.6 ± 6.6 | 100 ± 0 | ++ | + | + | + |
| (13) 2.5 | 0.1 | 88.0 ± 10.2 | 88.9 ± 0 | +(+) | +(+) | + | + |
| (14) 2.5 | 0.5 | 100 ± 0 | 100 ± 0 | ++ | + | + | + |

[a]Values represent means ± standard deviation of three replicates for each treatment.
[b]GP represents Golden Promise.
[c]GAL represents Galena.
[d]Morphology includes the degree of compactness and shine, from ++++, being the most compact and shiny callus to being the least compact and shiny callus.
[e]Color is from slightly brown (++++) to white (+).

TABLE 2

Regeneration of Golden Promise Calli Grown on CIM with Different Combinations of Auxins and Cytokinins

| Auxin Con. (mg/ml) | Cytokinin conc. (mg/ml) | 3rd Transfer | | 4th Transfer | | 5th Transfer | | 7th Transfer | | 9th Transfer | |
|---|---|---|---|---|---|---|---|---|---|---|---|
| | | NS[a] | NC[b] | NS | NC | NS | NC | NS | NC | NS | NC |
| Dicamba | BAP | | | | | | | | | | |
| 2.5 | 0 | 189 | 10 | 134 | 10 | 122 | 7 | 0 | 0 | 0 | 0 |
| 2.5 | 0.01 | 186 | 10 | 190 | 10 | 163 | 10 | 5 | 1 | 0 | 0 |
| 2.5 | 0.1 | 134 | 10 | 90 | 10 | 138 | 10 | 68 | 7 | 5 | 2 |
| 2.5 | 0.5 | 88 | 10 | 100 | 10 | 62 | 10 | 26 | 4 | 0 | 1 |
| 2,4-D | | | | | | | | | | | |
| 2.5 | 0 | 140 | 10 | 140 | 9 | 91 | 6 | 37 | 4 | 0 | 0 |
| 2.5 | 0.01 | 146 | 10 | 175 | 10 | 216 | 10 | 51 | 9 | 0 | 0 |
| 2.5 | 0.1 | 213 | 10 | 120 | 9 | 85 | 7 | 17 | 4 | 7 | 7 |
| 2.5 | 0.5 | 139 | 10 | 127 | 10 | 219 | 10 | 22 | 6 | 0 | 0 |
| Dicamba | Zeatin | | | | | | | | | | |
| 2.5 | 0.01 | 204 | 10 | 138 | 10 | 87 | 6 | 44 | 3 | 0 | 0 |
| 2.5 | 0.1 | 186 | 9 | 120 | 10 | 94 | 8 | 0 | 1 | 0 | 0 |
| 2.5 | 0.5 | 114 | 10 | 89 | 10 | 139 | 8 | 34 | 7 | 0 | 0 |
| 2,4-D | | | | | | | | | | | |
| 2.5 | 0.01 | 165 | 10 | 125 | 10 | 90 | 8 | 81 | 7 | 0 | 0 |
| 2.5 | 0.1 | 87 | 10 | 121 | 8 | 88 | 6 | 41 | 4 | 0 | 0 |
| 2.5 | 0.5 | 105 | 10 | 141 | 10 | 56 | 7 | 52 | 6 | 2 | 3 |

[a]NS = number of green shoots from 10 initial calli.
[b]NC = number of green shoots from 10 initial calli.

Example 2
High-Frequency Plant Regeneration from Transgenic and Nontransgenic Callus Tissues of Barley Materials and Methods.

Callus induction and maintenance. Callus induction was performed as described above using CIM with 2.5 mg/L of 2,4-D or dicamba (no cytokinin). After incubation for three weeks at 24+1° C. in the dark, callus was cut into small pieces (about 3 to 4 mm), then maintained on the same medium with subculturing at three-week intervals.

Plasmids. Plasmid ppGlbGus-6 (Liu, 1994) contains the uidA (gus) reporter gene under the control of the maize embryo-specific globulin (Glbl) promoter (containing 1.38 kb upstream of the transcription start site) and terminated by the *Agrobacterium tumefaciens* nopaline synthase 3' polyadenylation signal (nos). Plasmid pdGlbGUS-6 was constructed by (1) digesting ppGlblGUS with EcoRI to obtain a 2.54-kb fragment containing 0.37-kb of the globulin promoter, uidA reporter gene and nos terminator, and (2) ligating the 2.54-kb fragment into the vector pUC19. Plasmid pAHC20 contains the bar gene from *Streptomyces hygroscopicus* under the control of the maize ubiquitin Ubil promoter and first intron (Christensen and Quail, 1996) and followed by the 3'-untranslated region and nos.

Micro-projectile bombardment and transformation. Barley transformation via microparticle bombardment was carried out as described (Wan and Lemaux, 1994).

Recreneration via an intermediate-incubation step. Ten pieces of two-month-old nontransgenic calli grown on CIM supplemented with either 2,4-D or dicamba in the dark were transferred to RM either directly or following incubation on an IIM.

Two different IIM were used, DBC2 and DBC3. DBC2 medium is CIM containing 2.5 mg/L 2,4-D, 0.1 mg/L BAP, and 5.0 $\mu$M copper (Cupric sulfate). DBC3 medium is CIM containing 1.0 mg/L 2,4-D, 0.5 mg/L BAP, and 5.0 $\mu$M copper. After growing calli on these media for 3–4 weeks under dim light conditions (20 to 30 $\mu$E m$^{-2}$ s$^{-1}$; 16 h light/8 h dark), the numbers of calli producing green sectors or green regenerative structures were counted. Green sectors and small green regenerative structures were then transferred to fresh RM and grown under higher light intensity (45–55 $\mu$E m$^{-2}$ s$^{-1}$). After 3–4 weeks, the numbers of green shoots per callus piece were counted. For regeneration of transgenic callus lines, seven to ten pieces of transgenic calli were either transferred directly to each medium (containing 4–5 mg/L bialaphos) or transferred after an incubation on an IIM, then grown under the same conditions as described above for nontransgenic calli. Each treatment included four replicates of the regeneration test for nontransgenic calli but one replicate for transgenic calli.

Results

Transgenic calli and nontransgenic calli grown on the CIM with and without bialaphos, respectively, were transferred onto RM either directly or after incubation on an IIM. There was no significant difference among treatments in numbers of nontransgenic and transgenic calli of Golden Promise producing green sectors 3–4 weeks after transfer (Tables 4 and 6). Multiple green shoots were induced from-both transgenic and nontransgenic calli when either DBC2 or DBC3 was used as an IIM. Incubation on an IIM resulted in multiple green structures from 2,4-D and BAP and even more structures from the treatment including elevated levels of copper. Calli on either DBC2 or DBC3 formed multiple green shoots from the meristem-like structures; no albino plants were observed. Most of the green sectors that arose directly on RM without an intermediate incubation step regenerated fewer than two shoots per green sector, while green sectors grown on an IIM produced 2–5 shoots per green sector (Table 4). CIM containing 2,4-D was better in green-shoot regeneration than callus from medium containing dicamba (Table 4). The frequency of shoot regeneration was increased 5.6-fold to 6.4-fold for nontransgenic calli initiated and maintained on BCI-DM (barley callus-induction medium [Wan and Lemaux, 1994] containing 2.5 mg/L dicamba) with the use of an intermediate-incubation step (Table 4). Calli grown on BCI-2,4-D (barley callus induction medium [Wan and Lemaux, 1994] containing 2.5 mg/L 2,4-D) displayed a shoot regeneration frequency that was increased approximately 2.3-fold to 3.4-fold in response to the intermediate-incubation step. However, plantlets regenerated directly on RM grew faster than plantlets grown with an intermediate-incubation step.

Five independent transgenic lines at the fourth to sixth round of selection were tested for green shoot regeneration with or without an intermediate-incubation step (Table 6). The transgenic lines were obtained on selection medium (BCI-DM plus 5 mg/L bialaphos) then transferred onto FHG (+4 mg/L bialaphos) with or without an intermediate step. After 3–4 weeks, numbers of green spots were counted and regenerative tissues were transferred onto fresh FHG medium (+4 mg/L bialaphos). After an additional three weeks, numbers of green shoots were counted. The regenerability of green shoots varied depending upon the transgenic line; however, the frequency of green shoot regeneration from transgenic calli cultured with an intermediate-incubation step increased 2.8- to 11.4-fold (Table 6). Only line GPGlbGUS-13 line did not produce any green plants, even with an intermediate-incubation step.

Discussion

In this study, two different media, DBC2 and DBC3, were used for an intermediate-incubation step to improve the regenerability of transgenic and nontransgenic callus tissues of Golden Promise. No significant difference was detected among treatments in terms of numbers of transgenic and nontransgenic calli producing green sectors (Tables 4 and 6). However, transfer of tissue onto DBC2 or DBC3 induced the formation of multiple green structures, ultimately resulting in a greater number of plants, from each piece.

Calli grown on callus-induction-medium containing auxin alone (either 2,4-D or dicamba) produce green sectors or green structures from only small areas of each callus culture. In many cases, these green sectors do not generate plantlets on RM, possibly due to insufficient numbers of cells being generated on RM to give rise to entire plantlets. If An intermediate incubation step is used, the number of green sectors or structures that generate plantlets is increased. The use of 2,4-D in combination with BAP in the intermediate step might improve regeneration by allowing proliferation of green, totipotent cells capable of producing plants.

Nontransgenic barley callus grown on callus-induction medium containing 2,4-D or dicamba alone and transgenic callus selected on CIM containing dicamba and bialaphos produce multiple shoot meristem-like structures when subsequently transferred to intermediate incubation medium containing BAP, 2,4-D, and copper (50×) under dim light conditions (Tables 4 and 6). These meristem-like structures subsequently produce multiple shoots. In contrast, medium containing BAP alone produces only one or a few shoots per green sector. Thus, an IIM containing an appropriate auxin, BAP, and copper to treat callus promotes the production of multiple green meristem-like structures and resultant plantlets.

No significant difference in regenerability between DBC2 and DBC3 (Tables 4 and 6) is observed; rather, the callus structure itself determined the outcome. In general, DBC2 medium is more appropriate for callus with smaller-sized green sectors than DBC3 medium. DBC2 medium inhibits the growth of shoots, but green sectors or green structures can be maintained and proliferated on this medium for a long period of time until they have achieved a size appropriate for regeneration. Green tissues of Golden Promise, Galena, Harrington, and Salome, for example, can be maintained for more than 10 months (more than 4–6 months for Morex). These tissues produce multiple green shoots with a range of 9–17 shoots per piece of green tissue 4–6 mm in size. When germinating tissues were broken into 3–4 pieces after 3–4 weeks on RM and transferred to fresh medium, an even greater number of shoots were produced from the small embryogenic structures in which no shoots had yet formed.

Although the use of the intermediate-incubation step increased regenerability, there were still transformation events which were not regenerable. For example, the GPGlbGUS-13 transgenic line did not produce any green plants, possibly due to either transformation of a single original nonregenerable cell or to the early loss of regenerability during culturing of the callus. The use of an intermediate-incubation step as early as possible during the regeneration procedure also reduced the incidence of albinism. By applying this intermediate-incubation step at earlier selection stages, we obtained green, transgenic plants from a recalcitrant commercial cultivar called Galena, a result that was unachievable using published procedures.

Compared to earlier methods (Wan and Lemaux, 1994), the use of an intermediate-incubation step increased the frequency of shoot regeneration about 2.3-fold to about 11.4-fold for the nontransgenic and transgenic calli of Golden Promise and improved the culturability and regenerability of other recalcitrant commercially important genotypes, such as the North American malting cultivars Harrington and Morex (see Table 5).

TABLE 4

Regeneration of Nontransgenic Callus Tissues of Golden Promise

| Maintenance Medium | Intermediate Step | Regeneration Medium | Calli with Green Spots per Calli Tested | Green Shoots per Callus Piece |
|---|---|---|---|---|
| BCI-DM | FHG | FHG | 4.8 ± 3.6/10 | 0.35 ± 0.13 (100%) |
| | DBC2 | FHG | 5.5 ± 3.0/10 | 1.95 ± 0.26 (557%) |
| | DBC3 | FHG | 7.3 ± 1.0/10 | 2.23 ± 0.29 (637%) |
| BCI-2,4-D | FHG | FHG | 7.5 ± 1.7/10 | 1.15 ± 0.30 (100%) |
| | DBC2 | FHG | 7.8 ± 2.1/10 | 3.88 ± 1.36 (337%) |
| | DBC3 | FHG | 8.5 ± 0.6/10 | 2.6 ± 0.52 229% |

TABLE 5

Regeneration of Nontransgenic Callus Tissues of Morex

| Maintenance Medium | Intermediate Step | Regeneration Medium | Calli with Green Spots per Calli Tested | Shoots per Callus Piece Green | Shoots per Callus Piece Albino |
|---|---|---|---|---|---|
| BCI-2,4-D | FHG | FHG | 3.3/7 | 0 | 0 |
| | DBC2 | FHG | 3.7/7 | 0.29 | 2.4 |

TABLE 6

Regeneration of Transgenic Callus Tissues of Golden Promise

| Transgenic Line | Intermediate Step | Regeneration Medium | No. of Calli with Green Sports/No. of Calli Tested | No. of Green Shoots Per Callus |
|---|---|---|---|---|
| GPGlbGUS-6 | FHG | FHG | 6/10 | 0.1 (100%) |
| | DBC2[a] | FHG | 6/10 | 0.7 (700%) |
| | DBC3[b] | FHG | 7/10 | 0.4 (400%) |
| GPGlbGUS-7 | FHG | FHG | 6/7 | 0.43 (100%) |
| | DBC2 | FHG | 6/7 | 1.57 (365%) |
| | DBC3 | FHG | 4/7 | 3.29 (765%) |
| GPGlbGUS-13 | FHG | FHG | 0/10 | 0.0 (0%) |
| | DBC2 | FHG | 0/10 | 0.0 (0%) |
| | DBC3 | FHG | 0/10 | 0.0 (0%) |
| GPdGGUS-5 | FHG | FHG | 10/10 | 1.0 (100%) |
| | DBC2 | FHG | 10/10 | 4.9 (490%) |
| | DBC3 | FHG | 9/10 | 11.4 (1140%) |
| GPdGGUS-8 | FGH | FHG | 6/7 | 0.57 (100%) |
| | DBC2 | FHG | 5/7 | 2.14 (375%) |
| | DBC3 | FHG | 3/7 | 1.57 275% |

[a]DBC2 is CIM containing 2.5 mg/L 2,4-D, 0.1 mg/L BAP, 5.0 μM copper, plus 4 mg/L bialaphos.
[b]DBC3 is CIM containing 1.0 mg/L 2,4-D, 0.5 mg/L BAP, 5.0 μM copper, plus 4 mg/L bialaphos.

Example 3

Reduction of Genotype Limitation and Albinism: Transformation of Barley Genotype Golden Promise and the Recalcitrant Barley Genotype Galena Materials and Methods Plant Material. Donor plants for immature embryos were grown in soil under controlled conditions in growth chambers as described (Wan and Lemaux, 1994; Lemaux et al., 1996) or in the greenhouse, as noted (immature embryos grown in the growth chambers are preferred for green tissue culture, although it is not necessary to use greenhouse-grown plant material).

The greenhouse had supplementary lighting providing a 14-h photoperiod with temperatures of 15 to 18° C. Supplemental 1000-watt metal-halide lights were engaged when the light level in the greenhouse was less than 1000 $\mu E\ m^{-2}\ s^{-1}$. Roof shades covered the roof when outside light levels rose above 7000 $\mu E\ m^{-2}\ s^{-1}$.

Callus induction and green embryogenic tissue production. Immature zygotic embryos about 1.5 to 2.5 mm in size were dissected and isolated intact under a stereo dissecting microscope from seeds that were surface-sterilized for 10 min in 20% (v/v) bleach (5.25% sodium hypochlorite) followed by three washes in sterile water. The embryos were placed scutellum-side down on CIM.

Six different CIMs were used to test callus-induction frequencies and callus quality. The CIMs had, respectively, different concentrations of: 2,4-D (1.0 and 2.5 mg/L), BAP (0.01, 0.1 and 0.5 mg/L), and cupric sulfate ($CuSO_4$; 0.1 and 5.0 μM) as shown in Table 7.

DBC1 medium, which is CIM with 2.5 mg/L 2,4-D, 0.01 mg/L BAP, and 5.0 μM $CuSO_4$, was used for the initial callus-induction period with Golden Promise. DBC2 medium was used for the initial callus-induction period with Galena and Salome.

Five to seven days after callus initiation, germinating shoots and roots were removed from the callusing scutellum by manual excision. After 3–4 weeks initial incubation in the dark at 24±1° C., embryogenic callus from the scutellum was cut into small pieces (about 3–4 mm), transferred to fresh DBC2 medium (Golden Promise and Galena), and grown under dim light conditions (approximately 10 to 20 $\mu E\ m^{-2} s^{-1}$, 16 h-light). After an additional three weeks (at the second transfer), green callusing sectors were selected, broken into two to three pieces (each about 3–4 mm-in size) and transferred to fresh DBC2 medium.

Green regenerative tissues from Golden Promise and Salome were maintained on DBC2 medium, subculturing at three to four-week intervals.

DBC3 medium was used from the second transfer for Galena and subculturing took place at three to four-week intervals.

Plant regeneration. Seven pieces of four-month-old green regenerative tissue (about 4–6 mm) were plated on solid RM and exposed to a light intensity of approximately 30 to 50 $\mu$E m$^{-2}$s$^{-1}$. After 25-days, the numbers of green tissues that produced shoots and the numbers of shoots per piece of green tissue were counted. A single base of green tissue with more than one leaf was considered as one shoot.

Regenerated shoots were transferred to rooting medium (CI medium without hormones) in Magenta® boxes (Magenta Corporation, Chicago, Ill.). When the shoot reached the top of the box (approximately 3–4 weeks), plantlets were transferred to 6-inch pots containing Super-soil™ (R. McClellan, S. San Francisco, Calif.), gradually acclimatized, and grown to maturity in the greenhouse.

Plasmid. Plasmid pAHC25 includes the uidA (gus) reporter gene and a selectable gene, bar, each under control of the maize ubiquitin Ubi1 promoter and intron 1 and terminated by nos (Christensen and Quail, 1996).

DNA particle bombardment. Intact barley embryos were surface-sterilized, placed scutellum-side down, and grown on CIM, either supplemented with 2.5 mg/L 2,4-D and 5.0 $\mu$M CuSO$_4$ (DC medium) or supplemented with 2.5 mg/L 2,4-D and 0.1 $\mu$M CuSO$_4$ (D medium).

One day after excision of Galena embryos at 24±1° C. in the dark, the embryos were transferred scutellum-side up for osmotic pretreatment on CIM containing no maltose but including 0.2 M mannitol and 0.2 M sorbitol. Four hours after treatment with the osmoticum, the embryos were bombarded as described (Lemaux et al. 1996). Briefly, this involved the coating of 1 $\mu$m gold particles (Analytical Scientific Instruments, Alameda, Calif.) with plasmid DNA followed by bombardment using a PDS-1000 He biolistic device (Bio-Rad, Inc., Hercules, Calif.) at 900 psi 16–18 hours after bombardment, the embryos were placed scutellum-side down on DC medium (no bialaphos) and grown at 24+1° C. in the dark for 10–14 days.

Selection and regeneration of transformed tissue. Following an initial 10- to 14-day culturing period, each callusing embryo was broken into two or three pieces (approximately 4–5 mm each), depending on callus size, transferred to DBC2 medium supplemented with 4 mg/L bialaphos, and incubated in the dark. Two weeks after the second transfer (first-round selection), callus was transferred to new DBC2 medium containing 4 mg/L bialaphos, and 7 to 14 days later, calli were moved to dim light conditions (about 10 $\mu$E m$^{-2}$s$^{-1}$, 16 h-light). Through the fourth transfer, calli were maintained on the same medium. At the fifth transfer, calli were moved to DBC3 medium supplemented with 4 mg/L bialaphos. Cultures were subcultured at two-week intervals on DBC3 medium with 4 mg/L bialaphos until formation of green structures occurred, at which time they were plated on solid RM containing 3 mg/L bialaphos for regeneration and exposed to higher intensity light (approximately 30–50 $\mu$E m$^{-2}$ s$^{-1}$). After 3–4 weeks on RM, regenerated shoots were transferred to Magenta® boxes containing rooting medium (CI medium containing 0.1 $\mu$M copper without hormones) supplemented with 2–3 mg/L bialaphos. When the shoots reached the top of the box, plantlets were treated as described above.

Histochemical GUS assay. GUS activity was assayed histochemically as described (Jefferson et al., 1987).

PCR assay. Polymerase chain reaction (PCR) analysis was carried out using genomic DNA extracted from calli or leaves. Two sets of primers were used for confirming the presence of the bar gene, Bar5F and Bar1R (Lemaux et al., 1996). Another set of primers was used for confirming the presence of the gus gene, uidA1 and uidA2R (Cho et al., 1996). Amplifications were performed in a 25 $\mu$L reaction volume containing 10× PCR buffer, 25 mM MgCl$_2$, 2.5 mM dNTPs, 20 $\mu$M each primer, with 0.25 $\mu$L Taq DNA polymerase (Promega). Cycling was controlled by a thermal cycler programmed with the following conditions: 1 min denaturation step at 94° C.; 10 cycles at: 94° C. for 45 sec, 60° C. for 0.1–0.5 min/cycle, 72° C. for 1 min; and –26 cycles at: 94° C. for 45 sec, 55° C. for 1 min, 72° C. for 1 min. For the final cycle, the duration of the extension step was 7 min at 72° C. 25 $\mu$L of the PCR product with loading dye was electrophoresed on a 0.8% agarose gel with ethidium bromide and detected by UV light.

DNA hybridization analysis. Genomic DNA isolated from leaf tissue of a nontransformed control plant and T$_0$ and T$_1$, plants of transgenic lines was digested with XbaI and either SacI or PstI. Digestion with XbaI and SacI releases an intact 1.8 kb uidA (gus) fragment; digestion with XbaI and PstI releases an intact 0.6 kb bar fragment. For gel electrophoresis, each lane was loaded with 10 $\mu$g of each digest. After Southern transfer, the resulting blot was hybridized with a $^{32}$P-labeled uidA or bar probe.

Results

Initial callus induction and growth. The initial callus-induction frequency was determined using CIM of different compositions. Ten immature embryos from the barley genotypes Golden Promise and Galena were transferred to each CIM. Each CIM contained the following levels of hormones and copper: D, 2.5 mg/L 2,4-D and 0.1 $\mu$M CuSO$_4$; DC, 2.5 mg/L 2,4-D and 5.0 $\mu$M CuSO$_4$; DB, 2.5 mg/L 2,4-D, 0.1 mg/L BAP 0.1 $\mu$M CuSO$_4$; DBC1, 2.5 mg/L 2,4-D, 0.01 mg/L BAP and 5.0 $\mu$M CuSO$_4$; DBC2, 2.5 mg/L 2,4-D, 0.1 mg/L BAP and 5.0 $\mu$M CuSO$_4$; DBC3, 1.0 mg/L 2,4-D, 0.5 mg/L BAP and 5.0 $\mu$M, CuSO$_4$. Callus quality was assessed microscopically and scored on a scale with +++++ designating highest quality and + designating lowest quality. Values were measured three weeks after initial callus induction and represent means of three replicates for each treatment. Golden Promise had a high frequency of callus induction regardless of the CIM composition (>87%, Table 7). Galena had a high frequency of callus induction (>90%) on CIM without BAP. Tissue quality was poor on CIM containing BAP three weeks after induction but improved after two to three transfers on this medium. Only a fraction of scutellar tissues on Galena immature embryos formed callus, while most of the scutellar surface on Golden Promise immature embryos formed high-quality callus.

Galena had a similar or slightly higher initial callus growth rate compared to Golden Promise when grown on D medium (CIM containing 2,4-D alone) or DC medium (CIM containing 2,4-D and elevated levels of copper) (Table 7). Increasing the level of copper to 5.0 $\mu$M (50×) did not change the callus-induction frequency or the initial callus growth rate in either genotype, but callus quality improved, especially in Golden Promise. Compared to Galena, Golden Promise immature embryos produced callus with a larger number of distinct embryogenic structures.

The addition of BAP to the CIM reduced the callus-induction frequency and inhibited callus growth for both genotypes but produced higher quality callus that was shiny, compact, and contained highly regenerative structures with multiple shoot meristems (Table 7). Galena required a higher level of BAP (0.1 mg/L) than Golden Promise (0.01 mg/L BAP) to obtain callus of high quality (Table 7). The higher level of copper (50×) in combination with BAP resulted in more regenerative structures from callus having a slightly brownish color. When DBC3 medium, which contains a higher level of BAP (0.5 mg/L) and a lower level of 2,4-D (1.0 mg/L), was used for initial callus induction, a high rate of embryo germination and production of poor quality callus with a slow growth rate occurred (Table 7).

Production and maintenance of green regenerative tissues. Green embryogenic structures were observed 5–20 days after exposure of 3–4 week-old callus to dim light. A higher percentage of green sectors was produced by Golden Promise callus than Galena callus tissue. Once a callus having the appropriate morphology under dim light conditions was identified (green, shiny, nodular, compact), the sectors could be easily separated from the remaining callus and maintained on either DBC2 or DBC3 medium. Approximately 6–8 weeks post-initiation on DBC2 medium, Golden Promise tissue contained a few green shoots with multiple shoot meristem-like structures, but most tissues were green, shiny, nodular and compact. For Galena, however, DBC3 medium was optimal for maintaining green regenerative tissues. On DBC3 medium, Golden Promise tissues were softer and produced multiple shoot meristems; germination of some shoots was induced in response to a higher level of BAP. Galena tissues produced multiple shoot meristems and were more compact on DBC3 medium than Golden Promise tissues.

Thus, Galena requires a-higher level of BAP (0.5 mg/L) than Golden Promise (0.1 mg/L) for callus induction and maintenance of high-quality green regenerative tissues. It should be noted that in these experiments, the callus-induction media used do not contain a high level of copper. Callus morphology was very good with 0.1 mg/L BAP, but the growth rate was very slow. When 50× copper was added, it seemed to speed up the growth rate. A higher level of BAP in callus-induction medium containing 50× copper was needed for optimal growth of tissues compared with callus-induction medium containing 1× copper.

Fertile plant regeneration from green regenerative tissues. Seven pieces of green embryogenic tissues 4 to 6 mm in size from each genotype were transferred to RM (FHG medium), and after 25 days the number of regenerated shoots were counted. Each piece yielded multiple green shoots. After 2–3 weeks on RM, green structures (4–6 mm in size) from both genotypes produced approximately 9–17 green shoots per piece on either RM (Table 8) or hormone-free rooting medium. When germinating tissues were broken into pieces after 3–4 weeks in culture on RM and transferred to fresh medium, an even larger number of shoots were produced from the small green structures. All four-month-old green structures tested for regeneration produced multiple green shoots; no albino plants were observed (Table 8). Regenerated shoots were transferred to rooting medium in Magenta® boxes and rooted plants were transferred to soil and grown to maturity in the greenhouse.

Transformation of Galena. The in vitro culture system described above results in multiple green shoots from immature embryo-derived callus, thus providing the basis for successful transformation of the recalcitrant commercial genotype, Galena.

For transformation, the scutella of immature embryos of Galena were bombarded with subsequent culturing of the embryos on DC medium in the absence of selection. From the second transfer on, calli were maintained on selection medium; in the middle of the third round of transfer, calli-were moved to dim light. Media containing higher levels of BAP, lower levels of 2,4-D, and 50× copper (DBC3 medium) were used for selection and maintenance from the fifth transfer on. In general, bialaphos-resistant calli with green sectors were observed at the fourth to fifth transfer. Calli with green sectors were maintained and proliferated until the green sectors formed fully developed regenerative structures. In most cases, when green sectors developed in fast-growing callus, fully developed green regenerative structures could be obtained.

For Galena, embryo size was very important for callus induction. Embryos smaller than about 1.2 mm resulted in very poor callus induction (less than 20 percent). Immature embryos about 1.5 mm to 2.0 mm in size had the highest callus induction frequency (>90 percent).

This method of generating green structures that yield, multiple green shoots was used to improve the regenerability of transgenic calli selected on CIM containing either dicamba or 2,4-D. Green sectors were regenerated under selection and the plantlets were transferred to soil approximately three weeks after transfer to rooting medium. Using this transformation protocol, we obtained six independent Galena lines transformed with pAHC25. Three lines produced green sectors, were regenerable, and produced multiple green shoots. $T_0$ and $T_1$, plants contained DNA sequences that hybridized to bar and uidA and functionally expressed the uidA (GUS) reporter gene and the herbicide resistance gene bar as judged by resistance to Basta™.

Discussion

We have developed a very efficient, reproducible system for producing highly regenerative callus that gives rise to multiple green shoots over long periods of time (Table 8), eliminating the problem of albinism. This system can be successfully used to transform and regenerate previously recalcitrant genotypes.

First, we have optimized phytohormone treatment during callus initiation and proliferation. Immature embryos from Galena required higher levels of BAP than Golden Promise in order to produce high quality, green, regenerative tissue, perhaps due to differences between the two genotypes in endogenous levels of phytohormones. The addition of BAP to CIM containing 2,4-D decreased the growth rate of the immature embryo-derived callus from both genotypes but improved its quality and regenerability (Table 7). It is possible that the lack of albinism in this study was at least partially attributable to the use of BAP.

Recently, in vitro culture systems utilizing 2,4-D and BAP were developed for the differentiation of multiple shoots from excised shoot apical meristems from maize (Zhong et al., 1992) and oat (Zhang et al., 1996). We found that the sectors of regenerative barley calli of Golden Promise and Galena that were grown on CIM containing 2,4-D or dicamba produced multiple shoot meristem-like structures when subsequently transferred to an intermediate-incubation medium containing 2,4-D and BAP under dim light conditions. The use of 2,4-D in combination with BAP provided more prolonged regenerability and was more applicable to other genotypes than dicamba in combination with BAP.

Other changes in culture conditions significantly improved in vitro manipulation. Compared to D medium, DC medium, which includes increased levels of copper (5.0 µM, a 50-fold increase from MS medium), improved callus quality (Table 7) without changing callus-induction frequencies or the initial callus growth rate. This provided higher quality material from the initial step of selection that led to increased regenerablity in transformed tissues. In addition, the use of DBC2 medium at the second transfer of Galena resulted in higher quality tissue that produced multiple shoot meristem-like structures.

These results were consistent with studies indicating that 50 $\mu$M copper (500×) is optimal for regenerability of the barley variety Hector, while 5.0 $\mu$M is optimal for regenerability for the barley variety Excel (Dahleen, 1996). Similar results were reported for wheat, wherein regeneration was reportedly higher on medium containing 10 $\mu$M CuSO$_4$ (100×) than on MS (0.1 $\mu$M Cu$^{2+}$) (Purmhauser, 1991). In yet another study, an increased copper level resulted in more somatic embryoids from anthers of tetraploid wheat (Ghaemi et al., 1994).

The exposure of tissue to light early in the selection process also likely reduced the incidence of albinism, perhaps by inducing chlorophyll biosynthetic enzymes (Holtorf et al., 1995). The presence of green, regenerative sectors assures that green plants will be generated, thus decreasing or eliminating the regeneration of albino plants as observed in Wan and Lemaux (1994).

Shiny, compact, slightly brown-colored calli with highly regenerative structures were obtained 2–3 weeks after incubating embryos in the dark on CIM. For both genotypes, the calli were transferred to fresh medium containing BAP, 2,4-D and copper, and green embryogenic structures were formed 5–14 days after exposure to dim light. All four-month-old regenerative structures of both Golden Promise and Galena regenerated multiple green shoots (approximately 11–17 green shoots per callus piece, Table 8) and no albino plants. By contrast, four-month-old callus of Golden Promise and Galena maintained on CIM containing either 2.5 mg/L 2,4-D or dicamba alone did not produce green shoots (Example 1); even two-month-old callus of Golden Promise maintained on CIM containing 2,4-D or dicamba alone produced only 0.35 and 1.15 green shoots per callus piece, respectively (Example 2). These regenerative structures could be maintained on 2,4-D, BAP and copper for more than ten months in this state and could be regenerated to give multiple fertile green plants with both genotypes. The morphology of the green tissues generated by our protocol was similar to that of the multiple green meristematic domes differentiated from shoot apical meristems following culture on 2,4-D and BAP, but was more compact, possibly due to the inherent differences in the tissue source or to the use of higher concentrations of 2,4-D.

It has been reported that callus quality and callus-induction frequency depend on the selection of appropriately sized embryos and optimization of the physiological state of the donor plant (Dale and Dambrogio, 1979; Goldenstein and Kronstadt, 1986; Lürz and Lörz, 1987; Wan and Lemaux, 1994). However, the green regenerative tissues produced using our protocol can be obtained from a wider range of embryo sizes and from plants grown in either the growth chamber or the greenhouse; once green tissues are generated from any source, they can be proliferated as described. Small embryo size (<1.0 mm) was better in callus induction for Golden Promise, Morex, and Salome, but Galena required a larger size (1.5 to 2.0 mm) of embryos for a higher callus-induction frequency.

Many barley genotypes have a very low callus-induction frequency (Lürz and Lörz, 1987; Dahleen, 1996) and the appearance of albino plants and low regenerability occurs within 2.5 months after callus induction (Bregitzer et al., 1995). These traits limit the applicability of barley-transformation procedures for many modem commercial genotypes.

Previous efforts to transform the commercial varieties Moravian III and Galena produced large numbers of independently transformed lines, but yielded only albino plants upon regeneration. Changing the level of selection (to 1 mg/L bialaphos) or shortening the time of selection (from >5 rounds to 3 rounds) led to the regeneration of green plants that were found to be nontransformed.

The methods disclosed herein obviate the problems of albinism encountered with prolonged culture periods; in this study Galena and Golden Promise could be regenerated to give fertile green plants for more than 10 months. In addition, the use of either DBC2 or DBC3 in an intermediate step in regeneration greatly improves the frequency of shoot regeneration of transgenic and nontransgenic callus from Golden Promise initiated on 2,4-D or dicamba (Example 2).

Changes in particle bombardment, selection and culturing conditions, among others, also contributed to our transformation success with the previously recalcitrant genotype, Galena. Bombardments were previously carried out at 1100 psi, resulting in a reduction in callus-induction frequency in Galena, although Golden Promise was unaffected in its frequency. It is possible that lowering the rupture pressure and hence the speed of the microprojectiles lessened damage to the target tissue. In addition, selection of Galena was initiated two weeks post-bombardment rather than one day post-bombardment (Wan and Lemaux, 1994) in order to promote better callus induction and to allow for vigorous cell divisions of transformed cells without the adverse effects of the dead or dying cells in close proximity resulting from selection. Also, callusing embryos were broken into large pieces (4–5 mm) to avoid potential negative effects of wounding on transformed cells.

The approaches detailed herein can be used successfully to transform other recalcitrant commercial genotypes, such as the North American barley cultivars, Harrington, a two-row variety, and Morex, a six-row variety. Using these methods, Harrington and Morex produce green regenerative structures that yield multiple shoot meristems.

In addition, the ability to maintain green regenerative structures for long periods of time in culture permits the use of these structures as target tissues for transformation of cultivars prone to albinism, thus eliminating the need for maintaining donor plants and decreasing problems with albinism and poor regenerability, as well as reducing the induced mutation frequency and the resultant somaclonal variation.

TABLE 7

Callus-Induction-Frequency, Initial Callus Growth Rate and Callus Morpholocry of Golden Promise (GP) and Galena on Different Callus-Induction Media

| Genotype | Callus-Induction Medium | Initial Callus-Induction Frequency (%) | Growth Rate (mg/day/embryo) | Callus Morphology |
|---|---|---|---|---|
| GP | D | 100 | 12.8 | ++ |
| | DC | 100 | 10.6 | ++++ |
| | DB | 97 | 7.0 | +++(+) |
| | DBC1 | 100 | 11.5 | +++++ |
| | DBC2 | 100 | 9.1 | +++(+) |
| | DBC3 | 87 | 6.5 | ++ |
| Galena | D | 97 | 15.0 | + |
| | DC | 90 | 13.6 | +(+) |
| | DB | 67 | 5.7 | ++(+) |
| | DBC1 | 80 | 8.3 | ++ |
| | DBC2 | 47 | 5.8 | +++ |
| | DBC3 | 47 | 3.1 | ++ |

TABLE 8

Number of Shoots Regenerated from Green Embryogenic Tissues of Golden Promise and Galena

| Genotypes | Medium for Maintenance | # Regenerated Shoots/Green Tissue[c] | |
|---|---|---|---|
| | | Green | Albino |
| Golden Promise | DBC2[a] | 17.0 | 0 |
| Galena | DBC2 | 13.0 | 0 |
| Galena | DBC3[b] | 14.4 | 0 |

[a]DBC2 = CIM containing 2.5 mg/L 2,4-D, 0.1 mg/L BAP and 5.0 μM CuSO$_4$.
[b]DBC3 = CIM containing 1.0 mg/L 2,4-D, 0.5 mg/L BAP and 5.0 μM CuSO$_4$
[c]Values represent mean of three relicates for each treatment.

Example 4

Use of Green Regenerative Tissues of Barley as Transformation Targets Materials and Methods Plasmids. Plasmids pAHC20 and pAHC25 are described above. pAHC15 contains the GUS reporter gene expression cassette of pAHC25 (Christensen and Quail, 1996).

pUbiINPTII-1 was constructed by inserting the neomycin phosphotransferase (NPTII) coding sequence from pCaMVNEO (Fromm et al., 1986) into the BamHI site of pAHC17 which contains the maize ubiquitin Ubi1 promoter, Ubi1 intron 1, and the nos 3' terminator (Christensen and Quail, 1996).

Preparation of green regenerative tissues for DNA particle bombardment. Immature zygotic embryos were surface-sterilized, placed scutellum-side down on DBC2 medium, and incubated at 24±1° C. Regenerative tissues were maintained for 3–4 weeks, then cut into small pieces (about 3 to 5 mm), transferred to fresh DBC2 medium, and grown under dim light conditions. After an additional three weeks, green callusing sectors were broken into pieces (about 3 to 5 mm) and transferred to fresh DBC2 medium. Green regenerative tissues were maintained on DBC2 medium with subculturing at 3- to 4-week intervals. CIM containing 2.5 mg/L 2,4-D, 0.1 mg/L BAP and 5.0 μM CuSO$_4$ (i.e., DBC2 medium) was used for the induction of green regenerative tissues from the other genotypes.

For bombardment, green tissues (about 3 to 5 mm, four-months old) of Golden Promise and Galena were placed in the dark at 24±1° C. for one day, then transferred to DBC2 medium containing 0.2 M mannitol and 0.2 M sorbitol-. Four hours after treatment with the osmoticum, green tissues were bombarded as described (Lemaux et al. 1996) with gold particles (Analytical Scientific Instruments, Alameda, Calif.) coated with pAHC25, a mixture of pAHC20 and pAHC15, or a mixture of pUbiINPTII-1 and pAHC15 at 900 or 1100 psi. At 16–18 hours after bombardment, the green tissues were transferred to DBC2 medium without osmoticum and grown at 24±1° C. under dim light conditions (about 10 μE m$^{-2}$ s$^{-1}$, 16 h-light).

Selection and Regeneration of Transformed Tissue. Following an initial 3- to 4-week culturing period on nonselective medium, each piece of green tissue was broken into 1 to 2 pieces (about 4 mm to 5 mm, depending on size of original tissue piece) and transferred to DBC2 medium (Golden Promise or Galena) or DBC3 (Galena) medium supplemented with 4 to 6 mg/L bialaphos for bar selection or 40 to 50 mg/L geneticin (G418) for nptII selection. Green tissues were selected on DBC2 or DBC3 medium and 4 mm to 5 mm tissues subcultured at 3- to 4-week intervals. Putative green tissue transformants, identified by their fast-growth character on the selective medium, were transferred to Magenta® boxes containing rooting medium that was supplemented either with 4 mg/L bialaphos for bar selection or without selective agent for regeneration of nptII transformants. When shoots reached the top of the box, plantlets were transferred to 6-inch pots containing Supersoil (R. McClellan, S. San Francisco, Calif.), gradually acclimatized, and grown to maturity in the greenhouse.

Results and Discussion

Various targets have been used for barley transformation, including immature zygotic embryos (Wan and Lemaux, 1994; Hagio, et al., 1995), young callus (Wan and Lemaux, 1994), microspore-derived embryos (Wan and Lemaux, 1994), microspores (Jähne et al., 1994) and protoplasts (Funatsuki et al, 1995; Salmenkallio-Marttila et al., 1995). Immature zygotic embryos are currently the most widely used and reliable target tissue for barley transformation. However, immature embryos from most commercially important barley genotypes have low callus-induction response rates (Lürz and Lörz, 1987; Dahleen, 1996). Moreover, in vitro-derived tissue culture material is limited in its ability to yield green plants for prolonged periods (Bregitzer et al., 1995). Prolonged culturing periods and/or selection stress required during the transformation process result in a large proportion of albino (chlorophyll-deficient) plants (Foroughi-Wehr et al., 1982; Wan and Lemaux, 1994; Bregitzer et al., 1995). In addition, the use of immature embryos and microspores as target tissues requires the year-round maintenance of donor plants grown under defined growth conditions.

We have established a reproducible barley transformation system based on microprojectile bombardment of green tissues that utilizes an in vitro culture system for the production of multiple green shoots from callus derived from immature scutellar tissue. Selection commenced 3 to 4 weeks after bombardment to allow transformed cells to proliferate in the absence of dead or dying cells resulting from selection or wounding. From the second transfer, selection was started using DBC2 medium or DBC3 medium that was supplemented either with bialaphos for bar selection or G418 (geneticin) for nptII selection. Putative transformants identified after 3 to 4 rounds of selection were transferred to rooting medium supplemented with bialaphos.

Using this transformation protocol we have obtained one confirmed Golden Promise line transformed with pAHC20 plus pAHC15 following selection with bialaphos, plus one putative transformed Galena line with pUbiINPTII-1 plus pARC15 after G418 selection. Both lines were regenerable, producing green shoots and plants. Transformation was confirmed by PCR analysis.

This protocol greatly reduces problems with albinism and poor regeneration observed previously (Wan and Lemaux, 1994; Foroughi-Wehr et al., 1982; Bregitzer et al, 1995; Koprek et al, 1996; etc.) and can also be applied to other recalcitrant barley cultivars such as Harrington and Morex.

Example 5

Callus Morphology of Wheat on Different Callus Induction Media

The tissue culture protocols described above for use with barley are also useful for a variety of other plant species, including various monocot species.

For example, we have shown that the wheat variety Bobwhite also shows improved initial callus induction and callus morphology when tested on CIM containing high levels of copper and BAP. In experiments conducted as in Example 1 above (except as noted), immature whole embryos (1–2 mm) of Bobwhite were tested on six different CIMs, each including MS medium supplemented with 30 g/L maltose, 0.5 mg/L thiamine-HCl, 150 mg/L asparagine, and solidified with 2.5 g/L Phytagel (pH 5.85), and supplemented with copper and phytohormones as follows:

| (1) | WD: | 2.0 mg/L 2,4-D and 0.1 µM CuSO$_4$. |
|---|---|---|
| (2) | WDC: | 2.0 mg/L 2,4-D and 5.0 µM CuSO$_4$. |
| (3) | WDB: | 2.0 mg/L 2,4-D, 0.1 mg/L BAP, and 0.1 µM CuSO$_4$. |
| (4) | WDBC1: | 2.0 mg/L 2,4-D, 0.01 mg/L BAP, and 5.0 µM CuSO$_4$. |
| (5) | WDBC2: | 2.0 mg/L 2,4-D, 0.1 mg/L BAP, and 5.0 µM CuSO$_4$. |
| (4) | WDBC3: | 2.0 mg/L 2,4-D, 0.5 mg/L BAP, and 5.0 µM CuSO$_4$. |

The shoot apex was removed seven days after callus induction. The morphology of the callus induced on the media is shown in Table 9.

Having illustrated and described the principles of the present invention, it should be apparent to persons skilled in the art that the invention can be modified in arrangement and detail without departing from such principles. We claim all modifications that are within the spirit and scope of the appended claims.

TABLE 9

Callus Morpholocry of Bobwhite Wheat on Different, Callus-Induction Media

| Callus-Induction Medium | Callus Morphology[a] |
|---|---|
| WB | ++ |
| WDC | ++(+) |
| WDB | +++ |
| WDBC1 | +++ |
| WDBC2 | ++++ |
| WDBC3 | +++++ |

[a]Morphology ranges from + (watery, least compact, no regenerative meristem-like structures, white) to +++++ (least watery, most compact, multiple meristem-like structures).

REFERENCES

Ausubel et al., eds. (1992, with periodic updates) *Current Protocols in Molecular Biology*, Greene Publishing and Wiley-Interscience, New York.
Baillie et al. (1993) *Can. J. Plant Sci.* 73: 171–174.
Bhaskaran and Smith (1990) *Crop Sci.* 30:1328–1336.
Bregitzer (1992) *Crop Sci.* 32:1108–1112.
Bregitzer et al (1995) *Plant Cell Tiss. Org. Cult.* 43:229–235.
Breimann (1985) *Plant Cell Rep.* 4:161–163.
Christensen and Quail (1996) *Transgenic Res.* 5:1–6.
Dahleen (1996) *Plant Cell Tiss. Org. Cult.* 43:267–269.
Dale and Dambrogio (1979) *Z. Pflanzenphysiol.* 94:65–77.
De Block et al. (1987) *EMBO J.* 6:2513–2518.
Dmitrieva (1985) "Hormones, Dedifferentiation and Control of Proliferation in Cell and Protoplast Cultures," in: Butenko, ed., *Plant Cell Culture*, Biology Series, MIR Publishers, Moscow, pp. 35–50.
Fletcher (1969) *Planta* 89:1–8.
Foroughi-Wehr et al. (1982) *Theor. Appl. Genet.* 62: 233–239.
Fromm et al. (1986) *Nature* 319:791–793.
Fromm et al. (1989) *Plant Cell* 1:977.
Funatuski et al. (1995) *Theor. Appl. Genet.* 91:707–712.
Gelvin et al. (1990) *Plant Molecular Biology Manual*, Kluwer Academic Publishers.
Ghaemi et al. (1994) *Plant Cell Tiss. Org. Cult.* 36: 355–359.
Goldenstein and Kronstadt (1986) *Theor. Appl Genet.* 71:631–636.
Gordon-Karmm et al. (1990) *Plant Cell* 2:603.
Griffin and Dibble (1995) *Plant Cell Rep.* 14:721–724.
Hagio et al. (1995) *Plant Cell Rep.* 14:329–334.
Handel et al. (1985) *Crop Sci.* 25:27–31.
Holtorf et al. (1995) *Proc. Natl. Acad. Sci. USA* 92:3254–3258.
Hunter (1988) "Plant regeneration from microspores of barley, Hordeum vulgare," PhD thesis, Wye College, University of London, Ashford, Kent, England.
Jahne et al. (1991) *Plant Cell. Rep.* 10: 1–6.
Jahne et al. (1994) *Theor. Appl. Genet.* 89:525–533.
Jefferson et al. (1987) *EMBO LT.* 6:3901–3907.
Kao et al. (1991) *Plant Cell Rep.* 9:595–601.
Kasha et al. (1990) "Haploids in cereal improvement: Anther and microspore culture," in: *Gene manipulation in plant improvement:* 11, ed., Gustafson, Plenum, N.Y., pp. 213–235.
Koprek et al. (1996) *Plant Sci.* 119:79–91.
Kott and Kasha (1984) *Can. J. Bot.* 62:1245–1249.
Lemaux et al (1996) *Bombardment-mediated transformation methods for barley*, Bio-Rad US/EG Bulletin 2007.
Lewin (1994) *Genes V*, Oxford University Press: New York.
Liu (1994) *Analysis of ABA-Regulated Expression of the Maize GLB1 Gene in Tobacco Seeds and Maize Cells*, Ph.D. thesis, University of Illinois at Urbana-Champaign.
Lürz and Lörz (1987) *Theor. Appl. Genet.* 75:16–25.
Murakami et al. (1986) *Mol. Gen. Genet.* 205:42–50.
Murashige and Skoog (1962) *Physiol. Plant.* 15:473–497.
Pouwels et al. (1985, supp. 1987) *Cloning Vectors: A Laboratory Manual*.
Purnhauser (1991) *Cereal Res. Comm.* 19:419–423.
Rhagaran (1986) *Embryogenesis in Angiosperms*, Cambridge Univ. Press: Cambridge, p. 303.
Rieger et al. (1991) *Glossary of Genetics: Classical and Molecular*, 5th edition, Springer-Verlag__: New York.
Roshal et al. (1987) *EMBO LT.* 6:1155.
Salmenkallio-Marttila et al. (1995) *Plant Cell Rep.* 15:301–304.
Sambrook et al. (eds.) (1989), *Molecular Cloning: A Laboratory Manual*, 2nd ed., vol. 1–3, Cold Spring Harbor Laboratory Press: Cold Spring Harbor, N.Y.
Thomas and Scott (1985) *Plant Cell Rep.* 15:301–304.
Thompson et al. (1987) *EMBO J.* 6:2519–2523.
Tisserat (1985) "Embryogenesis, Organogenesis and Plant Regeneration," in: Dixon, ed., *Plant: Cell Culture: A Practical Approach*, Practical Approach Series, IRL Press, Oxford, Washington, D.C., pp. 79–105.
Vasil (1984) *Cell Culture and Somatic Cell Genetics of Plants*, Vols. I–III, Laboratory Procedures and Their Applications, Academic Press: New York.
Wan and Lemaux (1994) *Plant Physiol.* 104:37–48.
Weissbach and Weissbach (1989) *Methods for Plant Molecular Biology*, Academic Press: New York.
Wetmur and Davidson (1968) *J. Mol. Biol.* 31:349–370.
Zhang et al (1996) *J. Plant Physiol.* 148:667–671.
Zhong et al. (1991) *Plant Cell Rep.* 10:453–456.
Zhong et al. (1992) *Planta* 187:483–489.
Ziauddin and Kasha (1990) *Euphytica* 48:171–176.

What is claimed is:

1. A method of preparing green regenerative tissue of barley, suitable for transformation, comprising:
   incubating barley tissue on a callus-induction medium under dim light conditions for a sufficient time to produce green regenerative tissue, wherein the callus-induction medium comprises auxin at a concentration of about 0.1 mg/L to about 5 mg/L and copper at a concentration of about 0.1 µM to about 50 µM.

2. The method of claim 1, wherein the callus-induction medium further comprises cytokinin at a concentration of about 0.01 mg/L to about 2 mg/L.

3. The method of claim 2, wherein the auxin concentration is about 1 mg/L to about 2.5 mg/L and the cytokinin concentration is about 0.01 mg/L to about 0.5 mg/L.

4. The method of claim 2, wherein the auxin concentration is about 1 mg/L to about 2.5 mg/L, and the cytokinin is about 0.1 mg/L to about 2 mg/L.

5. The method of claim 1, wherein the auxin is selected from the group consisting of 2,4-dichlorophenoxyacetic acid, dicamba, naphthaleneacetic acid, indoleacetic acid, and mixtures thereof.

6. The method of claim 2, wherein the cytokinin is selected from the group consisting of 6-benzylaminopurine, zeatin, zeatin riboside, kinetin, 2iP, and mixtures thereof.

7. The method of claim 1, wherein the barley tissue is zygotic embryo tissue.

8. The method of claim 1, wherein the callus-induction medium further comprises maltose at a concentration which is capable of producing callus that is competent to form regenerative tissue.

9. The method of claim 1, wherein the barley tissue includes transformed barley cells.

10. The method of claim 1, wherein the green regenerative tissue is capable of being regenerated into a barley plant.

11. The method of claim 1 further comprising incubating the barley tissue on an intermediate-incubation medium, wherein the intermediate-induction medium comprises auxin at a concentration of about 0.1 mg/L to about 5 mg/L, cytokinin at a concentration of about 0.1 to about 5 mg/L and copper at a concentration of about 0.1 to about 50 µM.

12. The method of claim 11, wherein the auxin is selected from the group consisting of 2,4-dichlorophenoxyacetic acid, dicamba, naphthaleneaceetic acid, indoleacetic acid, and mixtures thereof.

13. The method of claim 11, wherein the cytokinin is selected from the group consisting of 6-benzylaminopurine, zeatin, zeatin riboside, kinetin, 2iP, and mixtures thereof.

14. The method of claim 11, wherein the intermediate-induction medium comprises auxin at a concentration of about 0.5 mg/L to about 2.5 mg/L.

15. The method of claim 11, wherein the intermediate-induction medium comprises maltose as a sugar source.

16. The method of claim 11, wherein the intermediate-induction medium comprises maltose at a concentration which is capable of proliferating the regenerative tissue.

17. The method of claim 11, wherein the barley tissue includes transformed barley cells.

18. The method of claim 11, wherein the intermediate-induction medium comprises maltose at a concentration which is capable of forming the regenerative tissue.

19. The method of claim 11, wherein the intermediate-induction medium comprises maltose at a concentration which is capable of forming and proliferating the regenerative tissue.

20. The method of claim 11, wherein the barley tissue is zygotic embryo tissue.

* * * * *

UNITED STATES PATENT AND TRADEMARK OFFICE
CERTIFICATE OF CORRECTION

| | | |
|---|---|---|
| PATENT NO. | : 6,541,257 B2 | Page 1 of 1 |
| APPLICATION NO. | : 09/825217 | |
| DATED | : April 1, 2003 | |
| INVENTOR(S) | : Peggy G. Lemaux et al. | |

It is certified that error appears in the above-identified patent and that said Letters Patent is hereby corrected as shown below:

At column 1, preceding line 4, please add the following statement:

--The research underlying this invention was supported with funds from USDA Grant No. CSRS 93-37500-9586. The U.S. Government may have certain rights.--

Signed and Sealed this

Thirty-first Day of July, 2007

JON W. DUDAS
*Director of the United States Patent and Trademark Office*